United States Patent [19]

Ebert et al.

[11] Patent Number: 5,688,677
[45] Date of Patent: Nov. 18, 1997

[54] DEOXYRIBONUCLEIC ACIDS CONTAINING INACTIVATED HORMONE RESPONSIVE ELEMENTS

[75] Inventors: Karl M. Ebert, Millbury; Paul DiTullio, Framingham; Seng Hing Cheng, Wellesley; Harry M. Meade, Newton; Alan Edward Smith, Dover, all of Mass.

[73] Assignee: Genzyme Corporation, Framingham, Mass.

[21] Appl. No.: 135,809

[22] Filed: Oct. 13, 1993

[51] Int. Cl.$^6$ .............................. C12N 15/06; C12N 15/12
[52] U.S. Cl. ...................... 435/240.1; 536/24.1; 536/23.5
[58] Field of Search ............................... 536/23.5, 24.1; 514/44; 435/6, 172.3, 240.1, 69.1; 800/2

[56] References Cited

U.S. PATENT DOCUMENTS 5,240,846  8/1993  Collins et al. ........................ 435/240.1

FOREIGN PATENT DOCUMENTS

| 91/02796 | 3/1991 | WIPO. |
| 91/10734 | 7/1991 | WIPO. |
| 93/12240 | 6/1993 | WIPO. |
| 93/12756 | 8/1993 | WIPO. |

OTHER PUBLICATIONS

Hyde, S.C. et al. (1993) "Correction of the Ion Transport Defect in Cystic Fibrosis Transgenic Mice by Gene Therapy" *Nature* 362:250–255.
Clarke, L.L. et al. (1992) "Defective Epithelial Chloride Transport in a Gene–Targeted Mouse Model of Cystic Fibrosis" *Science* 257:1125–1128.
Higgins, C.F. et al. (1992) "Cystic Fibrosis Mice Have Arrived" *Hum. Mol. Gen.* 1(7):459–460.
Snouwaert, J.N. et al. (1992) "An Animal Model For Cystic Fibrosis Made By Gene Targeting" *Science* 257:1083–1088.
Rosenfeld, M.A. et al. (1992) "In Vivo Transfer of the Human Cystic Fibrosis Transmembrane Conductance Regulator Gene to the Airway Epithelium" *Cell* 68:143–155.
Yoshimura, K. et al. (1992) "Expression of the Human Cystic Fibrosis Transmembrane Conductance Regulator Gene in the Mouse Lung After In Vivo Intratracheal Plasmid–Mediated Gene Transfer" *Nucleic Acids Res.* 20(12):3233–3240.
Smith, A.E. (1992) "Emerging Therapies for Cystic Fibrosis" Section V–Topics in Biology in *Ann. Rep. Med. Chem.* 27:235–243.
Anguiano, A. et al. (1992) "Congenital Bilateral Absence of the Vas Deferens: A Primarily Genital Form of Cystic Fibrosis" *JAMA* 267:1794–1797.
Anderson, M.P. et al. (1992) "Regulation by ATP and ADP of CFTR Chloride Channels That Contain Mutant Nucleotide–Binding Domains" *Science* 257:1701–1704.
Kartner, N. et al. (1991) "Expression of the Cystic Fibrosis Gene in Non–Epithelial Invertebrate Cells Produces a Regulated Anion Conductance" *Cell* 64:681–691j.

Koller, B.H. et al. (1991) "Toward an Animal Model of Cystic Fibrosis: Targeted Interruption of Exon 10 of the Cystic Fibrosis Transmembrane Regulator Gene in Embryonic Stem Cells" *Proc. Natl. Acad. Sci.* 88:10730–10734.
Rich D.P et al. (1991) "Effect of Deleting the R Domain on CFTR Generated Chloride Channels" *Science* 253:205–207.
Rosenfeld, M.A. et al. (1991) "In Vivo Transfer of the Human Cystic Fibrosis Gene to the Respiratory Epithelium" *Clin. Res.* 39(2):311 Aj.
Tsui, L–C. et al. (1991) "Biochemical and Molecular Genetics of Cystic Fibrosis" *Advances in Human Genetics* 20:153–266j.
Tabcharani, J.A. et al. (1991) "Phosphorylation–Regulated Cl–Channel in CHO Cells Stably Expressing the Cystic Fibrosis Gene" *Nature* 352:628–631.
Drumm, M.L. et al. (1990) "Correction of the Cystic Fibrosis Defect in Vitro By Retrovirus–Mediated Gene Transfer" *Cell* 62:1227–1233j.
Gregory, R.J. et al. (1990) "Expression and Chacterization of the Cystic Fibrosis Transmembrane Conductance Regulator" *Nature* 347:382–386j.
Rich, D.P. et al. (1990) "Expression of the Cystic Fibrosis Transmembrane Conductance Regulator Corrects Defective Chloride Channel Regulation in Cystic Fibrosis Airway Epithelial Cells" *Nature* 347:358–363j.
Huang, M.T.F. et al. (1990) "Intervening Sequences Increase Efficiency of RNA 3' Processing and Accumulation of Cytoplasmic RNA" *Nucleic Acids Res.* 18(4):937–947j.
Riordan, J.R. et al. (1989) "Identification of the Cystic Fibrosis Gene: Cloning and Characterization of Complementary DNA" *Science* 245:1066–1073j.
Rommens, J.H. et al. (1989) "Identification of the Cystic Fibrosis Gene: Chromosome Walking and Jumping" *Science* 245:1059–1065j.
Kerem, B.S. et al. (1989) "Identification of the Cystic Fibrosis Gene: Genetic Analysis" *Science* 245:1073–1080j.

*Primary Examiner*—James Martinell

[57] ABSTRACT

A DNA comprising at least one inactivated hormone responsive element and a nucleic acid sequence encoding a membrane-associated protein is described. Therapeutic compositions and cells including the DNA are also described. Other aspects of the invention include methods of treating subjects having cystic fibrosis which include administering an effective amount of the DNA to subjects having cystic fibrosis such that functional cystic fibrosis transmembrane conductance regulator is produced by the subject at a level which is not detrimental to the subject. The present invention also pertains to a method of introducing the DNA into a cell such that the membrane-associated protein is produced at a level which is not detrimental to the cell and cells produced by this method. Still other aspects of the invention include a method of assaying DNA for the presence or absence of a hormone responsive element in a species in which the hormone responsive element is functional and a method of selectively breeding female transgenic mammals which produce a protein of interest.

11 Claims, 14 Drawing Sheets

OTHER PUBLICATIONS

Yoshimura, K. et al. (1993) "Adenovirus–mediated Augmentation of Cell Transfection with Unmodified Plasmid Vectors" *J. Biol. Chem.* 268(4):2300–2303j.

Engelhardt, J.F. et al. (1993) "Direct Gene Transfer of Human CFTR into Human Bronchial Epithelia of Xenografts with E1–deleted Adenovirus" *Nat. Gen.* 4:27–34j.

Flotte, T.R. et al. (1993) "Expression of the Cystic Fibrosis Transmembrane Conductance Regulator from a Novel Adeno–associated Virus Promoter" *J. Biol. Chem.* 268(5):3781–3790j.

Johnson, L.G. et al. (1992) "Efficiency of Gene Transfer for Restoration of Normal Airway Epithelial Function in Cystic Fibrosis" *Nat. Gen.* 2:21–25.

Van Brunt, Bio/Technology 6: 1150 (1988).

Founder Animals

|  | Male | | Female | |
|---|---|---|---|---|
|  | Alive | Dead | Alive | Dead |
| Wild type-CFTR | 2 | 5 | 5 | 1 |
| Nonglycosylated-CFTR | 3 | 2 | 2 | 0 |
| Total | 5 | 7 | 7 | 1 |

F1 Animals

|  | Alive | Dead | Alive | Dead |
|---|---|---|---|---|
| Wild type-CFTR | 10 | 5 | 10 | 0 |
| Nonglycosylated-CFTR | 13 | 2 | 15 | 1 |
| Total | 23 | 7 | 25 | 1 |

FIGURE 12

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 6129 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 133..4572

( x i ) SEQUENCE DESCRIPTION: SEQ ID NO:1:

```
AATTGGAAGC AAATGACATC ACAGCAGGTC AGAGAAAAAG GGTTGAGCGG CAGGCACCCA        60

GAGTAGTAGG TCTTTGGCAT TAGGAGCTTG AGCCCAGACG GCCCTAGCAG GGACCCCAGC       120

GCCCGAGAGA CC ATG CAG AGG TCG CCT CTG GAA AAG GCC AGC GTT GTC           168
              Met Gln Arg Ser Pro Leu Glu Lys Ala Ser Val Val
                1               5                  10

TCC AAA CTT TTT TTC AGC TGG ACC AGA CCA ATT TTG AGG AAA GGA TAC         216
Ser Lys Leu Phe Phe Ser Trp Thr Arg Pro Ile Leu Arg Lys Gly Tyr
            15                  20                  25

AGA CAG CGC CTG GAA TTG TCA GAC ATA TAC CAA ATC CCT TCT GTT GAT         264
Arg Gln Arg Leu Glu Leu Ser Asp Ile Tyr Gln Ile Pro Ser Val Asp
        30                  35                  40

TCT GCT GAC AAT CTA TCT GAA AAA TTG GAA AGA GAA TGG GAT AGA GAG         312
Ser Ala Asp Asn Leu Ser Glu Lys Leu Glu Arg Glu Trp Asp Arg Glu
 45                 50                  55                  60

CTG GCT TCA AAG AAA AAT CCT AAA CTC ATT AAT GCC CTT CGG CGA TGT         360
Leu Ala Ser Lys Lys Asn Pro Lys Leu Ile Asn Ala Leu Arg Arg Cys
                65                  70                  75

TTT TTC TGG AGA TTT ATG TTC TAT GGA ATC TTT TTA TAT TTA GGG GAA         408
Phe Phe Trp Arg Phe Met Phe Tyr Gly Ile Phe Leu Tyr Leu Gly Glu
            80                  85                  90

GTC ACC AAA GCA GTA CAG CCT CTC TTA CTG GGA AGA ATC ATA GCT TCC         456
Val Thr Lys Ala Val Gln Pro Leu Leu Leu Gly Arg Ile Ile Ala Ser
            95                 100                 105

TAT GAC CCG GAT AAC AAG GAG GAA CGC TCT ATC GCG ATT TAT CTA GGC         504
Tyr Asp Pro Asp Asn Lys Glu Glu Arg Ser Ile Ala Ile Tyr Leu Gly
        110                 115                 120

ATA GGC TTA TGC CTT CTC TTT ATT GTG AGG ACA CTG CTC CTA CAC CCA         552
Ile Gly Leu Cys Leu Leu Phe Ile Val Arg Thr Leu Leu Leu His Pro
125                 130                 135                 140

GCC ATT TTT GGC CTT CAT CAC ATT GGA ATG CAG ATG AGA ATA GCT ATG         600
Ala Ile Phe Gly Leu His His Ile Gly Met Gln Met Arg Ile Ala Met
                145                 150                 155

TTT AGT TTG ATT TAT AAG AAG ACT TTA AAG CTG TCA AGC CGT GTT CTA         648
Phe Ser Leu Ile Tyr Lys Lys Thr Leu Lys Leu Ser Ser Arg Val Leu
            160                 165                 170

GAT AAA ATA AGT ATT GGA CAA CTT GTT AGT CTC CTT TCC AAC AAC CTG         696
Asp Lys Ile Ser Ile Gly Gln Leu Val Ser Leu Leu Ser Asn Asn Leu
        175                 180                 185

AAC AAA TTT GAT GAA GGA CTT GCA TTG GCA CAT TTC GTG TGG ATC GCT         744
Asn Lys Phe Asp Glu Gly Leu Ala Leu Ala His Phe Val Trp Ile Ala
    190                 195                 200
```

| | | | | | | | | | | | | | | | | |
|---|---|---|---|---|---|---|---|---|---|---|---|---|---|---|---|---|
| CCT | TTG | CAA | GTG | GCA | CTC | CTC | ATG | GGG | CTA | ATC | TGG | GAG | TTG | TTA | CAG | 792 |
| Pro | Leu | Gln | Val | Ala | Leu | Leu | Met | Gly | Leu | Ile | Trp | Glu | Leu | Leu | Gln | |
| 205 | | | | 210 | | | | | 215 | | | | | | 220 | |
| GCG | TCT | GCC | TTC | TGT | GGA | CTT | GGT | TTC | CTG | ATA | GTC | CTT | GCC | CTT | TTT | 840 |
| Ala | Ser | Ala | Phe | Cys | Gly | Leu | Gly | Phe | Leu | Ile | Val | Leu | Ala | Leu | Phe | |
| | | | | 225 | | | | | 230 | | | | | 235 | | |
| CAG | GCT | GGG | CTA | GGG | AGA | ATG | ATG | ATG | AAG | TAC | AGA | GAT | CAG | AGA | GCT | 888 |
| Gln | Ala | Gly | Leu | Gly | Arg | Met | Met | Met | Lys | Tyr | Arg | Asp | Gln | Arg | Ala | |
| | | | 240 | | | | | 245 | | | | | 250 | | | |
| GGG | AAG | ATC | AGT | GAA | AGA | CTT | GTG | ATT | ACC | TCA | GAA | ATG | ATT | GAA | AAT | 936 |
| Gly | Lys | Ile | Ser | Glu | Arg | Leu | Val | Ile | Thr | Ser | Glu | Met | Ile | Glu | Asn | |
| | | 255 | | | | | 260 | | | | | 265 | | | | |
| ATC | CAA | TCT | GTT | AAG | GCA | TAC | TGC | TGG | GAA | GAA | GCA | ATG | GAA | AAA | ATG | 984 |
| Ile | Gln | Ser | Val | Lys | Ala | Tyr | Cys | Trp | Glu | Glu | Ala | Met | Glu | Lys | Met | |
| | 270 | | | | | 275 | | | | | 280 | | | | | |
| ATT | GAA | AAC | TTA | AGA | CAA | ACA | GAA | CTG | AAA | CTG | ACT | CGG | AAG | GCA | GCC | 1032 |
| Ile | Glu | Asn | Leu | Arg | Gln | Thr | Glu | Leu | Lys | Leu | Thr | Arg | Lys | Ala | Ala | |
| 285 | | | | | 290 | | | | | 295 | | | | | 300 | |
| TAT | GTG | AGA | TAC | TTC | AAT | AGC | TCA | GCC | TTC | TTC | TTC | TCA | GGG | TTC | TTT | 1080 |
| Tyr | Val | Arg | Tyr | Phe | Asn | Ser | Ser | Ala | Phe | Phe | Phe | Ser | Gly | Phe | Phe | |
| | | | | 305 | | | | | 310 | | | | | 315 | | |
| GTG | GTG | TTT | TTA | TCT | GTG | CTT | CCC | TAT | GCA | CTA | ATC | AAA | GGA | ATC | ATC | 1128 |
| Val | Val | Phe | Leu | Ser | Val | Leu | Pro | Tyr | Ala | Leu | Ile | Lys | Gly | Ile | Ile | |
| | | | 320 | | | | | 325 | | | | | 330 | | | |
| CTC | CGG | AAA | ATA | TTC | ACC | ACC | ATC | TCA | TTC | TGC | ATT | GTT | CTG | CGC | ATG | 1176 |
| Leu | Arg | Lys | Ile | Phe | Thr | Thr | Ile | Ser | Phe | Cys | Ile | Val | Leu | Arg | Met | |
| | | 335 | | | | | 340 | | | | | 345 | | | | |
| GCG | GTC | ACT | CGG | CAA | TTT | CCC | TGG | GCT | GTA | CAA | ACA | TGG | TAT | GAC | TCT | 1224 |
| Ala | Val | Thr | Arg | Gln | Phe | Pro | Trp | Ala | Val | Gln | Thr | Trp | Tyr | Asp | Ser | |
| | 350 | | | | | 355 | | | | | 360 | | | | | |
| CTT | GGA | GCA | ATA | AAC | AAA | ATA | CAG | GAT | TTC | TTA | CAA | AAG | CAA | GAA | TAT | 1272 |
| Leu | Gly | Ala | Ile | Asn | Lys | Ile | Gln | Asp | Phe | Leu | Gln | Lys | Gln | Glu | Tyr | |
| 365 | | | | | 370 | | | | | 375 | | | | | 380 | |
| AAG | ACA | TTG | GAA | TAT | AAC | TTA | ACG | ACT | ACA | GAA | GTA | GTG | ATG | GAG | AAT | 1320 |
| Lys | Thr | Leu | Glu | Tyr | Asn | Leu | Thr | Thr | Thr | Glu | Val | Val | Met | Glu | Asn | |
| | | | | 385 | | | | | 390 | | | | | 395 | | |
| GTA | ACA | GCC | TTC | TGG | GAG | GAG | GGA | TTT | GGG | GAA | TTA | TTT | GAG | AAA | GCA | 1368 |
| Val | Thr | Ala | Phe | Trp | Glu | Glu | Gly | Phe | Gly | Glu | Leu | Phe | Glu | Lys | Ala | |
| | | | 400 | | | | | 405 | | | | | 410 | | | |
| AAA | CAA | AAC | AAT | AAC | AAT | AGA | AAA | ACT | TCT | AAT | GGT | GAT | GAC | AGC | CTC | 1416 |
| Lys | Gln | Asn | Asn | Asn | Asn | Arg | Lys | Thr | Ser | Asn | Gly | Asp | Asp | Ser | Leu | |
| | | 415 | | | | | 420 | | | | | 425 | | | | |
| TTC | TTC | AGT | AAT | TTC | TCA | CTT | CTT | GGT | ACT | CCT | GTC | CTG | AAA | GAT | ATT | 1464 |
| Phe | Phe | Ser | Asn | Phe | Ser | Leu | Leu | Gly | Thr | Pro | Val | Leu | Lys | Asp | Ile | |
| | | 430 | | | | | 435 | | | | | 440 | | | | |
| AAT | TTC | AAG | ATA | GAA | AGA | GGA | CAG | TTG | TTG | GCG | GTT | GCT | GGA | TCC | ACT | 1512 |
| Asn | Phe | Lys | Ile | Glu | Arg | Gly | Gln | Leu | Leu | Ala | Val | Ala | Gly | Ser | Thr | |
| 445 | | | | | 450 | | | | | 455 | | | | | 460 | |
| GGA | GCA | GGC | AAG | ACT | TCA | CTT | CTA | ATG | ATG | ATT | ATG | GGA | GAA | CTG | GAG | 1560 |
| Gly | Ala | Gly | Lys | Thr | Ser | Leu | Leu | Met | Met | Ile | Met | Gly | Glu | Leu | Glu | |
| | | | | 465 | | | | | 470 | | | | | 475 | | |
| CCT | TCA | GAG | GGT | AAA | ATT | AAG | CAC | AGT | GGA | AGA | ATT | TCA | TTC | TGT | TCT | 1608 |
| Pro | Ser | Glu | Gly | Lys | Ile | Lys | His | Ser | Gly | Arg | Ile | Ser | Phe | Cys | Ser | |
| | | | 480 | | | | | 485 | | | | | 490 | | | |
| CAG | TTT | TCC | TGG | ATT | ATG | CCT | GGC | ACC | ATT | AAA | GAA | AAT | ATC | ATC | TTT | 1656 |
| Gln | Phe | Ser | Trp | Ile | Met | Pro | Gly | Thr | Ile | Lys | Glu | Asn | Ile | Ile | Phe | |
| | | 495 | | | | | 500 | | | | | 505 | | | | |
| GGT | GTT | TCC | TAT | GAT | GAA | TAT | AGA | TAC | AGA | AGC | GTC | ATC | AAA | GCA | TGC | 1704 |
| Gly | Val | Ser | Tyr | Asp | Glu | Tyr | Arg | Tyr | Arg | Ser | Val | Ile | Lys | Ala | Cys | |
| | | 510 | | | | | 515 | | | | | 520 | | | | |

-continued

| | | | | | | | | | | | | | | | | |
|---|---|---|---|---|---|---|---|---|---|---|---|---|---|---|---|---|
| CAA | CTA | GAA | GAG | GAC | ATC | TCC | AAG | TTT | GCA | GAG | AAA | GAC | AAT | ATA | GTT | 1752 |
| Gln | Leu | Glu | Glu | Asp | Ile | Ser | Lys | Phe | Ala | Glu | Lys | Asp | Asn | Ile | Val | |
| 525 | | | | 530 | | | | | 535 | | | | | | 540 | |
| CTT | GGA | GAA | GGT | GGA | ATC | ACA | CTG | AGT | GGA | GGT | CAA | CGA | GCA | AGA | ATT | 1800 |
| Leu | Gly | Glu | Gly | Gly | Ile | Thr | Leu | Ser | Gly | Gly | Gln | Arg | Ala | Arg | Ile | |
| | | | | 545 | | | | | 550 | | | | | 555 | | |
| TCT | TTA | GCA | AGA | GCA | GTA | TAC | AAA | GAT | GCT | GAT | TTG | TAT | TTA | TTA | GAC | 1848 |
| Ser | Leu | Ala | Arg | Ala | Val | Tyr | Lys | Asp | Ala | Asp | Leu | Tyr | Leu | Leu | Asp | |
| | | | 560 | | | | | 565 | | | | | 570 | | | |
| TCT | CCT | TTT | GGA | TAC | CTA | GAT | GTT | TTA | ACA | GAA | AAA | GAA | ATA | TTT | GAA | 1896 |
| Ser | Pro | Phe | Gly | Tyr | Leu | Asp | Val | Leu | Thr | Glu | Lys | Glu | Ile | Phe | Glu | |
| | | 575 | | | | | 580 | | | | | 585 | | | | |
| AGC | TGT | GTC | TGT | AAA | CTG | ATG | GCT | AAC | AAA | ACT | AGG | ATT | TTG | GTC | ACT | 1944 |
| Ser | Cys | Val | Cys | Lys | Leu | Met | Ala | Asn | Lys | Thr | Arg | Ile | Leu | Val | Thr | |
| | | 590 | | | | | 595 | | | | | 600 | | | | |
| TCT | AAA | ATG | GAA | CAT | TTA | AAG | AAA | GCT | GAC | AAA | ATA | TTA | ATT | TTG | CAT | 1992 |
| Ser | Lys | Met | Glu | His | Leu | Lys | Lys | Ala | Asp | Lys | Ile | Leu | Ile | Leu | His | |
| 605 | | | | | 610 | | | | | 615 | | | | | 620 | |
| GAA | GGT | AGC | AGC | TAT | TTT | TAT | GGG | ACA | TTT | TCA | GAA | CTC | CAA | AAT | CTA | 2040 |
| Glu | Gly | Ser | Ser | Tyr | Phe | Tyr | Gly | Thr | Phe | Ser | Glu | Leu | Gln | Asn | Leu | |
| | | | | 625 | | | | | 630 | | | | | 635 | | |
| CAG | CCA | GAC | TTT | AGC | TCA | AAA | CTC | ATG | GGA | TGT | GAT | TCT | TTC | GAC | CAA | 2088 |
| Gln | Pro | Asp | Phe | Ser | Ser | Lys | Leu | Met | Gly | Cys | Asp | Ser | Phe | Asp | Gln | |
| | | | 640 | | | | | 645 | | | | | 650 | | | |
| TTT | AGT | GCA | GAA | AGA | AGA | AAT | TCA | ATC | CTA | ACT | GAG | ACC | TTA | CAC | CGT | 2136 |
| Phe | Ser | Ala | Glu | Arg | Arg | Asn | Ser | Ile | Leu | Thr | Glu | Thr | Leu | His | Arg | |
| | | 655 | | | | | 660 | | | | | 665 | | | | |
| TTC | TCA | TTA | GAA | GGA | GAT | GCT | CCT | GTC | TCC | TGG | ACA | GAA | ACA | AAA | AAA | 2184 |
| Phe | Ser | Leu | Glu | Gly | Asp | Ala | Pro | Val | Ser | Trp | Thr | Glu | Thr | Lys | Lys | |
| 670 | | | | | 675 | | | | | 680 | | | | | | |
| CAA | TCT | TTT | AAA | CAG | ACT | GGA | GAG | TTT | GGG | GAA | AAA | AGG | AAG | AAT | TCT | 2232 |
| Gln | Ser | Phe | Lys | Gln | Thr | Gly | Glu | Phe | Gly | Glu | Lys | Arg | Lys | Asn | Ser | |
| 685 | | | | | 690 | | | | | 695 | | | | | 700 | |
| ATT | CTC | AAT | CCA | ATC | AAC | TCT | ATA | CGA | AAA | TTT | TCC | ATT | GTG | CAA | AAG | 2280 |
| Ile | Leu | Asn | Pro | Ile | Asn | Ser | Ile | Arg | Lys | Phe | Ser | Ile | Val | Gln | Lys | |
| | | | 705 | | | | | 710 | | | | | 715 | | | |
| ACT | CCC | TTA | CAA | ATG | AAT | GGC | ATC | GAA | GAG | GAT | TCT | GAT | GAG | CCT | TTA | 2328 |
| Thr | Pro | Leu | Gln | Met | Asn | Gly | Ile | Glu | Glu | Asp | Ser | Asp | Glu | Pro | Leu | |
| | | | 720 | | | | | 725 | | | | | 730 | | | |
| GAG | AGA | AGG | CTG | TCC | TTA | GTA | CCA | GAT | TCT | GAG | CAG | GGA | GAG | GCG | ATA | 2376 |
| Glu | Arg | Arg | Leu | Ser | Leu | Val | Pro | Asp | Ser | Glu | Gln | Gly | Glu | Ala | Ile | |
| | | 735 | | | | | 740 | | | | | 745 | | | | |
| CTG | CCT | CGC | ATC | AGC | GTG | ATC | AGC | ACT | GGC | CCC | ACG | CTT | CAG | GCA | CGA | 2424 |
| Leu | Pro | Arg | Ile | Ser | Val | Ile | Ser | Thr | Gly | Pro | Thr | Leu | Gln | Ala | Arg | |
| | | 750 | | | | | 755 | | | | | 760 | | | | |
| AGG | AGG | CAG | TCT | GTC | CTG | AAC | CTG | ATG | ACA | CAC | TCA | GTT | AAC | CAA | GGT | 2472 |
| Arg | Arg | Gln | Ser | Val | Leu | Asn | Leu | Met | Thr | His | Ser | Val | Asn | Gln | Gly | |
| 765 | | | | | 770 | | | | | 775 | | | | | 780 | |
| CAG | AAC | ATT | CAC | CGA | AAG | ACA | ACA | GCA | TCC | ACA | CGA | AAA | GTG | TCA | CTG | 2520 |
| Gln | Asn | Ile | His | Arg | Lys | Thr | Thr | Ala | Ser | Thr | Arg | Lys | Val | Ser | Leu | |
| | | | | 785 | | | | | 790 | | | | | 795 | | |
| GCC | CCT | CAG | GCA | AAC | TTG | ACT | GAA | CTG | GAT | ATA | TAT | TCA | AGA | AGG | TTA | 2568 |
| Ala | Pro | Gln | Ala | Asn | Leu | Thr | Glu | Leu | Asp | Ile | Tyr | Ser | Arg | Arg | Leu | |
| | | | 800 | | | | | 805 | | | | | 810 | | | |
| TCT | CAA | GAA | ACT | GGC | TTG | GAA | ATA | AGT | GAA | GAA | ATT | AAC | GAA | GAA | GAC | 2616 |
| Ser | Gln | Glu | Thr | Gly | Leu | Glu | Ile | Ser | Glu | Glu | Ile | Asn | Glu | Glu | Asp | |
| | | 815 | | | | | 820 | | | | | 825 | | | | |
| TTA | AAG | GAG | TGC | CTT | TTT | GAT | GAT | ATG | GAG | AGC | ATA | CCA | GCA | GTG | ACT | 2664 |
| Leu | Lys | Glu | Cys | Leu | Phe | Asp | Asp | Met | Glu | Ser | Ile | Pro | Ala | Val | Thr | |
| | | 830 | | | | | 835 | | | | | 840 | | | | |

| | | | | | | | | | | | | | | | | |
|---|---|---|---|---|---|---|---|---|---|---|---|---|---|---|---|---|
| ACA | TGG | AAC | ACA | TAC | CTT | CGA | TAT | ATT | ACT | GTC | CAC | AAG | AGC | TTA | ATT | 2712 |
| Thr | Trp | Asn | Thr | Tyr | Leu | Arg | Tyr | Ile | Thr | Val | His | Lys | Ser | Leu | Ile | |
| 845 | | | | 850 | | | | | 855 | | | | | | 860 | |
| TTT | GTG | CTA | ATT | TGG | TGC | TTA | GTA | ATT | TTT | CTG | GCA | GAG | GTG | GCT | GCT | 2760 |
| Phe | Val | Leu | Ile | Trp | Cys | Leu | Val | Ile | Phe | Leu | Ala | Glu | Val | Ala | Ala | |
| | | | | 865 | | | | | 870 | | | | | 875 | | |
| TCT | TTG | GTT | GTG | CTG | TGG | CTC | CTT | GGA | AAC | ACT | CCT | CTT | CAA | GAC | AAA | 2808 |
| Ser | Leu | Val | Val | Leu | Trp | Leu | Leu | Gly | Asn | Thr | Pro | Leu | Gln | Asp | Lys | |
| | | | 880 | | | | | 885 | | | | | | 890 | | |
| GGG | AAT | AGT | ACT | CAT | AGT | AGA | AAT | AAC | AGC | TAT | GCA | GTG | ATT | ATC | ACC | 2856 |
| Gly | Asn | Ser | Thr | His | Ser | Arg | Asn | Asn | Ser | Tyr | Ala | Val | Ile | Ile | Thr | |
| | | 895 | | | | | 900 | | | | | 905 | | | | |
| AGC | ACC | AGT | TCG | TAT | TAT | GTG | TTT | TAC | ATT | TAC | GTG | GGA | GTA | GCC | GAC | 2904 |
| Ser | Thr | Ser | Ser | Tyr | Tyr | Val | Phe | Tyr | Ile | Tyr | Val | Gly | Val | Ala | Asp | |
| | 910 | | | | | 915 | | | | | | 920 | | | | |
| ACT | TTG | CTT | GCT | ATG | GGA | TTC | TTC | AGA | GGT | CTA | CCA | CTG | GTG | CAT | ACT | 2952 |
| Thr | Leu | Leu | Ala | Met | Gly | Phe | Phe | Arg | Gly | Leu | Pro | Leu | Val | His | Thr | |
| 925 | | | | | 930 | | | | | 935 | | | | | 940 | |
| CTA | ATC | ACA | GTG | TCG | AAA | ATT | TTA | CAC | CAC | AAA | ATG | TTA | CAT | TCT | GTT | 3000 |
| Leu | Ile | Thr | Val | Ser | Lys | Ile | Leu | His | His | Lys | Met | Leu | His | Ser | Val | |
| | | | | 945 | | | | | 950 | | | | | | 955 | |
| CTT | CAA | GCA | CCT | ATG | TCA | ACC | CTC | AAC | ACG | TTG | AAA | GCA | GGT | GGG | ATT | 3048 |
| Leu | Gln | Ala | Pro | Met | Ser | Thr | Leu | Asn | Thr | Leu | Lys | Ala | Gly | Gly | Ile | |
| | | | 960 | | | | | 965 | | | | | 970 | | | |
| CTT | AAT | AGA | TTC | TCC | AAA | GAT | ATA | GCA | ATT | TTG | GAT | GAC | CTT | CTG | CCT | 3096 |
| Leu | Asn | Arg | Phe | Ser | Lys | Asp | Ile | Ala | Ile | Leu | Asp | Asp | Leu | Leu | Pro | |
| | | 975 | | | | | 980 | | | | | 985 | | | | |
| CTT | ACC | ATA | TTT | GAC | TTC | ATC | CAG | TTG | TTA | TTA | ATT | GTG | ATT | GGA | GCT | 3144 |
| Leu | Thr | Ile | Phe | Asp | Phe | Ile | Gln | Leu | Leu | Leu | Ile | Val | Ile | Gly | Ala | |
| | 990 | | | | | 995 | | | | | | 1000 | | | | |
| ATA | GCA | GTT | GTC | GCA | GTT | TTA | CAA | CCC | TAC | ATC | TTT | GTT | GCA | ACA | GTG | 3192 |
| Ile | Ala | Val | Val | Ala | Val | Leu | Gln | Pro | Tyr | Ile | Phe | Val | Ala | Thr | Val | |
| 1005 | | | | | 1010 | | | | | 1015 | | | | | 1020 | |
| CCA | GTG | ATA | GTG | GCT | TTT | ATT | ATG | TTG | AGA | GCA | TAT | TTC | CTC | CAA | ACC | 3240 |
| Pro | Val | Ile | Val | Ala | Phe | Ile | Met | Leu | Arg | Ala | Tyr | Phe | Leu | Gln | Thr | |
| | | | | 1025 | | | | | 1030 | | | | | | 1035 | |
| TCA | CAG | CAA | CTC | AAA | CAA | CTG | GAA | TCT | GAA | GGC | AGG | AGT | CCA | ATT | TTC | 3288 |
| Ser | Gln | Gln | Leu | Lys | Gln | Leu | Glu | Ser | Glu | Gly | Arg | Ser | Pro | Ile | Phe | |
| | | | | 1040 | | | | | 1045 | | | | | | 1050 | |
| ACT | CAT | CTT | GTT | ACA | AGC | TTA | AAA | GGA | CTA | TGG | ACA | CTT | CGT | GCC | TTC | 3336 |
| Thr | His | Leu | Val | Thr | Ser | Leu | Lys | Gly | Leu | Trp | Thr | Leu | Arg | Ala | Phe | |
| | | | 1055 | | | | | 1060 | | | | | 1065 | | | |
| GGA | CGG | CAG | CCT | TAC | TTT | GAA | ACT | CTG | TTC | CAC | AAA | GCT | CTG | AAT | TTA | 3384 |
| Gly | Arg | Gln | Pro | Tyr | Phe | Glu | Thr | Leu | Phe | His | Lys | Ala | Leu | Asn | Leu | |
| | | 1070 | | | | | 1075 | | | | | 1080 | | | | |
| CAT | ACT | GCC | AAC | TGG | TTC | TTG | TAC | CTG | TCA | ACA | CTG | CGC | TGG | TTC | CAA | 3432 |
| His | Thr | Ala | Asn | Trp | Phe | Leu | Tyr | Leu | Ser | Thr | Leu | Arg | Trp | Phe | Gln | |
| 1085 | | | | | 1090 | | | | | 1095 | | | | | 1100 | |
| ATG | AGA | ATA | GAA | ATG | ATT | TTT | GTC | ATC | TTC | TTC | ATT | GCT | GTT | ACC | TTC | 3480 |
| Met | Arg | Ile | Glu | Met | Ile | Phe | Val | Ile | Phe | Phe | Ile | Ala | Val | Thr | Phe | |
| | | | | 1105 | | | | | 1110 | | | | | | 1115 | |
| ATT | TCC | ATT | TTA | ACA | ACA | GGA | GAA | GGA | GAA | GGA | AGA | GTT | GGT | ATT | ATC | 3528 |
| Ile | Ser | Ile | Leu | Thr | Thr | Gly | Glu | Gly | Glu | Gly | Arg | Val | Gly | Ile | Ile | |
| | | | | 1120 | | | | | 1125 | | | | | 1130 | | |
| CTG | ACT | TTA | GCC | ATG | AAT | ATC | ATG | AGT | ACA | TTG | CAG | TGG | GCT | GTA | AAC | 3576 |
| Leu | Thr | Leu | Ala | Met | Asn | Ile | Met | Ser | Thr | Leu | Gln | Trp | Ala | Val | Asn | |
| | | | 1135 | | | | | 1140 | | | | | 1145 | | | |
| TCC | AGC | ATA | GAT | GTG | GAT | AGC | TTG | ATG | CGA | TCT | GTG | AGC | CGA | GTC | TTT | 3624 |
| Ser | Ser | Ile | Asp | Val | Asp | Ser | Leu | Met | Arg | Ser | Val | Ser | Arg | Val | Phe | |
| | | 1150 | | | | | 1155 | | | | | 1160 | | | | |

| | | | | | | | | | | | | | | | | |
|---|---|---|---|---|---|---|---|---|---|---|---|---|---|---|---|---|
| AAG | TTC | ATT | GAC | ATG | CCA | ACA | GAA | GGT | AAA | CCT | ACC | AAG | TCA | ACC | AAA | 3672 |
| Lys | Phe | Ile | Asp | Met | Pro | Thr | Glu | Gly | Lys | Pro | Thr | Lys | Ser | Thr | Lys | |
| 1165 | | | | 1170 | | | | | 1175 | | | | | | 1180 | |
| CCA | TAC | AAG | AAT | GGC | CAA | CTC | TCG | AAA | GTT | ATG | ATT | ATT | GAG | AAT | TCA | 3720 |
| Pro | Tyr | Lys | Asn | Gly | Gln | Leu | Ser | Lys | Val | Met | Ile | Ile | Glu | Asn | Ser | |
| | | | | 1185 | | | | | 1190 | | | | | 1195 | | |
| CAC | GTG | AAG | AAA | GAT | GAC | ATC | TGG | CCC | TCA | GGG | GGC | CAA | ATG | ACT | GTC | 3768 |
| His | Val | Lys | Lys | Asp | Asp | Ile | Trp | Pro | Ser | Gly | Gly | Gln | Met | Thr | Val | |
| | | 1200 | | | | | 1205 | | | | | 1210 | | | | |
| AAA | GAT | CTC | ACA | GCA | AAA | TAC | ACA | GAA | GGT | GGA | AAT | GCC | ATA | TTA | GAG | 3816 |
| Lys | Asp | Leu | Thr | Ala | Lys | Tyr | Thr | Glu | Gly | Gly | Asn | Ala | Ile | Leu | Glu | |
| | | | 1215 | | | | | 1220 | | | | | 1225 | | | |
| AAC | ATT | TCC | TTC | TCA | ATA | AGT | CCT | GGC | CAG | AGG | GTG | GGC | CTC | TTG | GGA | 3864 |
| Asn | Ile | Ser | Phe | Ser | Ile | Ser | Pro | Gly | Gln | Arg | Val | Gly | Leu | Leu | Gly | |
| | | 1230 | | | | | 1235 | | | | | 1240 | | | | |
| AGA | ACT | GGA | TCA | GGG | AAG | AGT | ACT | TTG | TTA | TCA | GCT | TTT | TTG | AGA | CTA | 3912 |
| Arg | Thr | Gly | Ser | Gly | Lys | Ser | Thr | Leu | Leu | Ser | Ala | Phe | Leu | Arg | Leu | |
| 1245 | | | | | 1250 | | | | | 1255 | | | | | 1260 | |
| CTG | AAC | ACT | GAA | GGA | GAA | ATC | CAG | ATC | GAT | GGT | GTG | TCT | TGG | GAT | TCA | 3960 |
| Leu | Asn | Thr | Glu | Gly | Glu | Ile | Gln | Ile | Asp | Gly | Val | Ser | Trp | Asp | Ser | |
| | | | | | 1265 | | | | | 1270 | | | | | 1275 | |
| ATA | ACT | TTG | CAA | CAG | TGG | AGG | AAA | GCC | TTT | GGA | GTG | ATA | CCA | CAG | AAA | 4008 |
| Ile | Thr | Leu | Gln | Gln | Trp | Arg | Lys | Ala | Phe | Gly | Val | Ile | Pro | Gln | Lys | |
| | | | 1280 | | | | | 1285 | | | | | 1290 | | | |
| GTA | TTT | ATT | TTT | TCT | GGA | ACA | TTT | AGA | AAA | AAC | TTG | GAT | CCC | TAT | GAA | 4056 |
| Val | Phe | Ile | Phe | Ser | Gly | Thr | Phe | Arg | Lys | Asn | Leu | Asp | Pro | Tyr | Glu | |
| | | | 1295 | | | | | 1300 | | | | | 1305 | | | |
| CAG | TGG | AGT | GAT | CAA | GAA | ATA | TGG | AAA | GTT | GCA | GAT | GAG | GTT | GGG | CTC | 4104 |
| Gln | Trp | Ser | Asp | Gln | Glu | Ile | Trp | Lys | Val | Ala | Asp | Glu | Val | Gly | Leu | |
| | | | 1310 | | | | | 1315 | | | | | 1320 | | | |
| AGA | TCT | GTG | ATA | GAA | CAG | TTT | CCT | GGG | AAG | CTT | GAC | TTT | GTC | CTT | GTG | 4152 |
| Arg | Ser | Val | Ile | Glu | Gln | Phe | Pro | Gly | Lys | Leu | Asp | Phe | Val | Leu | Val | |
| 1325 | | | | | 1330 | | | | | 1335 | | | | | 1340 | |
| GAT | GGG | GGC | TGT | GTC | CTA | AGC | CAT | GGC | CAC | AAG | CAG | TTG | ATG | TGC | TTG | 4200 |
| Asp | Gly | Gly | Cys | Val | Leu | Ser | His | Gly | His | Lys | Gln | Leu | Met | Cys | Leu | |
| | | | | 1345 | | | | | 1350 | | | | | 1355 | | |
| GCT | AGA | TCT | GTT | CTC | AGT | AAG | GCG | AAG | ATC | TTG | CTG | CTT | GAT | GAA | CCC | 4248 |
| Ala | Arg | Ser | Val | Leu | Ser | Lys | Ala | Lys | Ile | Leu | Leu | Leu | Asp | Glu | Pro | |
| | | | | 1360 | | | | | 1365 | | | | | 1370 | | |
| AGT | GCT | CAT | TTG | GAT | CCA | GTA | ACA | TAC | CAA | ATA | ATT | AGA | AGA | ACT | CTA | 4296 |
| Ser | Ala | His | Leu | Asp | Pro | Val | Thr | Tyr | Gln | Ile | Ile | Arg | Arg | Thr | Leu | |
| | | 1375 | | | | | 1380 | | | | | 1385 | | | | |
| AAA | CAA | GCA | TTT | GCT | GAT | TGC | ACA | GTA | ATT | CTC | TGT | GAA | CAC | AGG | ATA | 4344 |
| Lys | Gln | Ala | Phe | Ala | Asp | Cys | Thr | Val | Ile | Leu | Cys | Glu | His | Arg | Ile | |
| | | 1390 | | | | | 1395 | | | | | 1400 | | | | |
| GAA | GCA | ATG | CTG | GAA | TGC | CAA | CAA | TTT | TTG | GTC | ATA | GAA | GAG | AAC | AAA | 4392 |
| Glu | Ala | Met | Leu | Glu | Cys | Gln | Gln | Phe | Leu | Val | Ile | Glu | Glu | Asn | Lys | |
| 1405 | | | | 1410 | | | | | 1415 | | | | | | 1420 | |
| GTG | CGG | CAG | TAC | GAT | TCC | ATC | CAG | AAA | CTG | CTG | AAC | GAG | AGG | AGC | CTC | 4440 |
| Val | Arg | Gln | Tyr | Asp | Ser | Ile | Gln | Lys | Leu | Leu | Asn | Glu | Arg | Ser | Leu | |
| | | | | 1425 | | | | | 1430 | | | | | 1435 | | |
| TTC | CGG | CAA | GCC | ATC | AGC | CCC | TCC | GAC | AGG | GTG | AAG | CTC | TTT | CCC | CAC | 4488 |
| Phe | Arg | Gln | Ala | Ile | Ser | Pro | Ser | Asp | Arg | Val | Lys | Leu | Phe | Pro | His | |
| | | | 1440 | | | | | 1445 | | | | | 1450 | | | |
| CGG | AAC | TCA | AGC | AAG | TGC | AAG | TCT | AAG | CCC | CAG | ATT | GCT | GCT | CTG | AAA | 4536 |
| Arg | Asn | Ser | Ser | Lys | Cys | Lys | Ser | Lys | Pro | Gln | Ile | Ala | Ala | Leu | Lys | |
| | | | 1455 | | | | | 1460 | | | | | 1465 | | | |
| GAG | GAG | ACA | GAA | GAA | GAG | GTG | CAA | GAT | ACA | AGG | CTT | TAGAGAGCAG | | | | 4582 |
| Glu | Glu | Thr | Glu | Glu | Glu | Val | Gln | Asp | Thr | Arg | Leu | | | | | |
| 1470 | | | | 1475 | | | | | 1480 | | | | | | | |

-continued

| | | | | | |
|---|---|---|---|---|---|
| CATAAATGTT | GACATGGGAC | ATTTGCTCAT | GGAATTGGAG | CTCGTGGGAC | AGTCACCTCA | 4642 |
| TGGAATTGGA | GCTCGTGGAA | CAGTTACCTC | TGCCTCAGAA | AACAAGGATG | AATTAAGTTT | 4702 |
| TTTTTTAAAA | AAGAAACATT | TGGTAAGGGG | AATTGAGGAC | ACTGATATGG | GTCTTGATAA | 4762 |
| ATGGCTTCCT | GGCAATAGTC | AAATTGTGTG | AAAGGTACTT | CAAATCCTTG | AAGATTTACC | 4822 |
| ACTTGTGTTT | TGCAAGCCAG | ATTTTCCTGA | AAACCCTTGC | CATGTGCTAG | TAATTGGAAA | 4882 |
| GGCAGCTCTA | AATGTCAATC | AGCCTAGTTG | ATCAGCTTAT | TGTCTAGTGA | AACTCGTTAA | 4942 |
| TTTGTAGTGT | TGGAGAAGAA | CTGAAATCAT | ACTTCTTAGG | GTTATGATTA | AGTAATGATA | 5002 |
| ACTGGAAACT | TCAGCGGTTT | ATATAAGCTT | GTATTCCTTT | TTCTCTCCTC | TCCCCATGAT | 5062 |
| GTTTAGAAAC | ACAACTATAT | TGTTTGCTAA | GCATTCCAAC | TATCTCATTT | CCAAGCAAGT | 5122 |
| ATTAGAATAC | CACAGGAACC | ACAAGACTGC | ACATCAAAAT | ATGCCCCATT | CAACATCTAG | 5182 |
| TGAGCAGTCA | GGAAAGAGAA | CTTCCAGATC | CTGGAAATCA | GGGTTAGTAT | TGTCCAGGTC | 5242 |
| TACCAAAAAT | CTCAATATTT | CAGATAATCA | CAATACATCC | CTTACCTGGG | AAAGGGCTGT | 5302 |
| TATAATCTTT | CACAGGGGAC | AGGATGGTTC | CCTTGATGAA | GAAGTTGATA | TGCCTTTTCC | 5362 |
| CAACTCCAGA | AAGTGACAAG | CTCACAGACC | TTTGAACTAG | AGTTTAGCTG | GAAAAGTATG | 5422 |
| TTAGTGCAAA | TTGTCACAGG | ACAGCCCTTC | TTTCCACAGA | AGCTCCAGGT | AGAGGGTGTG | 5482 |
| TAAGTAGATA | GGCCATGGGC | ACTGTGGGTA | GACACACATG | AAGTCCAAGC | ATTTAGATGT | 5542 |
| ATAGGTTGAT | GGTGGTATGT | TTTCAGGCTA | GATGTATGTA | CTTCATGCTG | TCTACACTAA | 5602 |
| GAGAGAATGA | GAGACACACT | GAAGAAGCAC | CAATCATGAA | TTAGTTTTAT | ATGCTTCTGT | 5662 |
| TTTATAATTT | TGTGAAGCAA | AATTTTTTCT | CTAGGAAATA | TTTATTTTAA | TAATGTTTCA | 5722 |
| AACATATATT | ACAATGCTGT | ATTTTAAAAG | AATGATTATG | AATTACATTT | GTATAAAATA | 5782 |
| ATTTTTATAT | TTGAAATATT | GACTTTTTAT | GGCACTAGTA | TTTTTATGAA | ATATTATGTT | 5842 |
| AAAACTGGGA | CAGGGGAGAA | CCTAGGGTGA | TATTAACCAG | GGGCCATGAA | TCACCTTTTG | 5902 |
| GTCTGGAGGG | AAGCTTGGG | GCTGATCGAG | TTGTTGCCCA | CAGCTGTATG | ATTCCCAGCC | 5962 |
| AGACACAGCC | TCTTAGATGC | AGTTCTGAAG | AAGATGGTAC | CACCAGTCTG | ACTGTTTCCA | 6022 |
| TCAAGGGTAC | ACTGCCTTCT | CAACTCCAAA | CTGACTCTTA | AGAAGACTGC | ATTATATTTA | 6082 |
| TTACTGTAAG | AAAATATCAC | TTGTCAATAA | AATCCATACA | TTTGTGT | | 6129 |

( 2 ) INFORMATION FOR SEQ ID NO:2:

( i ) SEQUENCE CHARACTERISTICS:
        ( A ) LENGTH: 1480 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
```

|  |  |  | 85 |  |  |  |  | 90 |  |  |  |  | 95 |  |  |
|---|---|---|---|---|---|---|---|---|---|---|---|---|---|---|---|
| Val | Gln | Pro | Leu<br>100 | Leu | Leu | Gly | Arg | Ile<br>105 | Ile | Ala | Ser | Tyr<br>110 | Asp | Pro | Asp |
| Asn | Lys | Glu<br>115 | Glu | Arg | Ser | Ile | Ala<br>120 | Ile | Tyr | Leu | Gly | Ile<br>125 | Gly | Leu | Cys |
| Leu | Leu<br>130 | Phe | Ile | Val | Arg | Thr<br>135 | Leu | Leu | His | Pro | Ala<br>140 | Ile | Phe | Gly |
| Leu | His | His | Ile | Gly | Met | Gln | Met | Arg | Ile | Ala | Met | Phe | Ser | Leu | Ile |
| 145 |  |  |  |  | 150 |  |  |  |  | 155 |  |  |  |  | 160 |
| Tyr | Lys | Lys | Thr | Leu<br>165 | Lys | Leu | Ser | Ser | Arg<br>170 | Val | Leu | Asp | Lys | Ile<br>175 | Ser |
| Ile | Gly | Gln | Leu<br>180 | Val | Ser | Leu | Leu | Ser<br>185 | Asn | Asn | Leu | Asn | Lys<br>190 | Phe | Asp |
| Glu | Gly | Leu<br>195 | Ala | Leu | Ala | His | Phe<br>200 | Val | Trp | Ile | Ala | Pro<br>205 | Leu | Gln | Val |
| Ala | Leu<br>210 | Leu | Met | Gly | Leu | Ile<br>215 | Trp | Glu | Leu | Leu | Gln<br>220 | Ala | Ser | Ala | Phe |
| Cys<br>225 | Gly | Leu | Gly | Phe | Leu<br>230 | Ile | Val | Leu | Ala | Leu<br>235 | Phe | Gln | Ala | Gly | Leu<br>240 |
| Gly | Arg | Met | Met | Met<br>245 | Lys | Tyr | Arg | Asp | Gln<br>250 | Arg | Ala | Gly | Lys | Ile<br>255 | Ser |
| Glu | Arg | Leu | Val<br>260 | Ile | Thr | Ser | Glu | Met<br>265 | Ile | Glu | Asn | Ile | Gln<br>270 | Ser | Val |
| Lys | Ala | Tyr<br>275 | Cys | Trp | Glu | Glu | Ala<br>280 | Met | Glu | Lys | Met | Ile<br>285 | Glu | Asn | Leu |
| Arg | Gln<br>290 | Thr | Glu | Leu | Lys | Leu<br>295 | Thr | Arg | Lys | Ala | Ala<br>300 | Tyr | Val | Arg | Tyr |
| Phe | Asn | Ser | Ser | Ala | Phe | Phe | Phe | Ser | Gly | Phe | Phe | Val | Val | Phe | Leu |
| 305 |  |  |  |  | 310 |  |  |  |  | 315 |  |  |  |  | 320 |
| Ser | Val | Leu | Pro | Tyr<br>325 | Ala | Leu | Ile | Lys | Gly<br>330 | Ile | Ile | Leu | Arg | Lys<br>335 | Ile |
| Phe | Thr | Thr | Ile<br>340 | Ser | Phe | Cys | Ile | Val<br>345 | Leu | Arg | Met | Ala | Val<br>350 | Thr | Arg |
| Gln | Phe | Pro<br>355 | Trp | Ala | Val | Gln | Thr<br>360 | Trp | Tyr | Asp | Ser | Leu<br>365 | Gly | Ala | Ile |
| Asn | Lys<br>370 | Ile | Gln | Asp | Phe | Leu<br>375 | Gln | Lys | Gln | Glu | Tyr<br>380 | Lys | Thr | Leu | Glu |
| Tyr<br>385 | Asn | Leu | Thr | Thr | Thr<br>390 | Glu | Val | Val | Met | Glu<br>395 | Asn | Val | Thr | Ala | Phe<br>400 |
| Trp | Glu | Glu | Gly | Phe<br>405 | Gly | Glu | Leu | Phe | Glu<br>410 | Lys | Ala | Lys | Gln | Asn<br>415 | Asn |
| Asn | Asn | Arg | Lys<br>420 | Thr | Ser | Asn | Gly | Asp<br>425 | Asp | Ser | Leu | Phe | Phe<br>430 | Ser | Asn |
| Phe | Ser | Leu<br>435 | Leu | Gly | Thr | Pro | Val<br>440 | Leu | Lys | Asp | Ile | Asn<br>445 | Phe | Lys | Ile |
| Glu | Arg<br>450 | Gly | Gln | Leu | Leu | Ala<br>455 | Val | Ala | Gly | Ser | Thr<br>460 | Gly | Ala | Gly | Lys |
| Thr<br>465 | Ser | Leu | Leu | Met | Met<br>470 | Ile | Met | Gly | Glu | Leu<br>475 | Glu | Pro | Ser | Glu | Gly<br>480 |
| Lys | Ile | Lys | His | Ser<br>485 | Gly | Arg | Ile | Ser | Phe<br>490 | Cys | Ser | Gln | Phe | Ser<br>495 | Trp |
| Ile | Met | Pro | Gly<br>500 | Thr | Ile | Lys | Glu | Asn<br>505 | Ile | Ile | Phe | Gly | Val<br>510 | Ser | Tyr |

| | | | | | | | | | | | | | |
|---|---|---|---|---|---|---|---|---|---|---|---|---|---|
|Asp|Glu|Tyr 515|Arg|Tyr|Arg|Ser|Val 520|Ile|Lys|Ala|Cys|Gln 525|Leu|Glu|Glu|
|Asp|Ile 530|Ser|Lys|Phe|Ala|Glu 535|Lys|Asp|Asn|Ile|Val 540|Leu|Gly|Glu|Gly|
|Gly 545|Ile|Thr|Leu|Ser|Gly 550|Gly|Gln|Arg|Ala|Arg 555|Ile|Ser|Leu|Ala|Arg 560|
|Ala|Val|Tyr|Lys|Asp 565|Ala|Asp|Leu|Tyr|Leu 570|Leu|Asp|Ser|Pro|Phe 575|Gly|
|Tyr|Leu|Asp|Val 580|Leu|Thr|Glu|Lys|Glu 585|Ile|Phe|Glu|Ser|Cys 590|Val|Cys|
|Lys|Leu|Met 595|Ala|Asn|Lys|Thr|Arg 600|Ile|Leu|Val|Thr|Ser 605|Lys|Met|Glu|
|His|Leu 610|Lys|Lys|Ala|Asp|Lys 615|Ile|Leu|Ile|Leu|His 620|Glu|Gly|Ser|Ser|
|Tyr 625|Phe|Tyr|Gly|Thr|Phe 630|Ser|Glu|Leu|Gln|Asn 635|Leu|Gln|Pro|Asp|Phe 640|
|Ser|Ser|Lys|Leu|Met 645|Gly|Cys|Asp|Ser|Phe 650|Asp|Gln|Phe|Ser|Ala 655|Glu|
|Arg|Arg|Asn|Ser 660|Ile|Leu|Thr|Glu|Thr 665|Leu|His|Arg|Phe|Ser 670|Leu|Glu|
|Gly|Asp|Ala 675|Pro|Val|Ser|Trp|Thr 680|Glu|Thr|Lys|Lys|Gln 685|Ser|Phe|Lys|
|Gln|Thr 690|Gly|Glu|Phe|Gly|Glu 695|Lys|Arg|Lys|Asn|Ser 700|Ile|Leu|Asn|Pro|
|Ile 705|Asn|Ser|Ile|Arg|Lys 710|Phe|Ser|Ile|Val|Gln 715|Lys|Thr|Pro|Leu|Gln 720|
|Met|Asn|Gly|Ile|Glu 725|Glu|Asp|Ser|Asp|Glu 730|Pro|Leu|Glu|Arg|Arg 735|Leu|
|Ser|Leu|Val|Pro 740|Asp|Ser|Glu|Gln|Gly 745|Glu|Ala|Ile|Leu|Pro 750|Arg|Ile|
|Ser|Val|Ile 755|Ser|Thr|Gly|Pro|Thr 760|Leu|Gln|Ala|Arg|Arg 765|Arg|Gln|Ser|
|Val|Leu 770|Asn|Leu|Met|Thr|His 775|Ser|Val|Asn|Gln|Gly 780|Gln|Asn|Ile|His|
|Arg 785|Lys|Thr|Thr|Ala|Ser 790|Thr|Arg|Lys|Val|Ser 795|Leu|Ala|Pro|Gln|Ala 800|
|Asn|Leu|Thr|Glu|Leu 805|Asp|Ile|Tyr|Ser|Arg 810|Arg|Leu|Ser|Gln|Glu 815|Thr|
|Gly|Leu|Glu|Ile 820|Ser|Glu|Glu|Ile|Asn 825|Glu|Glu|Asp|Leu|Lys 830|Glu|Cys|
|Leu|Phe|Asp 835|Asp|Met|Glu|Ser|Ile 840|Pro|Ala|Val|Thr|Thr 845|Trp|Asn|Thr|
|Tyr|Leu 850|Arg|Tyr|Ile|Thr|Val 855|His|Lys|Ser|Leu|Ile 860|Phe|Val|Leu|Ile|
|Trp 865|Cys|Leu|Val|Ile|Phe 870|Leu|Ala|Glu|Val|Ala 875|Ala|Ser|Leu|Val|Val 880|
|Leu|Trp|Leu|Leu|Gly 885|Asn|Thr|Pro|Leu|Gln 890|Asp|Lys|Gly|Asn|Ser 895|Thr|
|His|Ser|Arg|Asn 900|Asn|Ser|Tyr|Ala|Val 905|Ile|Ile|Thr|Ser|Thr 910|Ser|Ser|
|Tyr|Tyr|Val 915|Phe|Tyr|Ile|Tyr|Val 920|Gly|Val|Ala|Asp|Thr 925|Leu|Leu|Ala|
|Met|Gly 930|Phe|Phe|Arg|Gly|Leu 935|Pro|Leu|Val|His|Thr 940|Leu|Ile|Thr|Val|

```
Ser  Lys  Ile  Leu  His  His  Lys  Met  Leu  His  Ser  Val  Leu  Gln  Ala  Pro
945                 950                 955                 960

Met  Ser  Thr  Leu  Asn  Thr  Leu  Lys  Ala  Gly  Gly  Ile  Leu  Asn  Arg  Phe
                    965                 970                 975

Ser  Lys  Asp  Ile  Ala  Ile  Leu  Asp  Asp  Leu  Leu  Pro  Leu  Thr  Ile  Phe
               980                 985                 990

Asp  Phe  Ile  Gln  Leu  Leu  Leu  Ile  Val  Ile  Gly  Ala  Ile  Ala  Val  Val
          995                 1000                1005

Ala  Val  Leu  Gln  Pro  Tyr  Ile  Phe  Val  Ala  Thr  Val  Pro  Val  Ile  Val
          1010                1015                1020

Ala  Phe  Ile  Met  Leu  Arg  Ala  Tyr  Phe  Leu  Gln  Thr  Ser  Gln  Gln  Leu
1025                1030                1035                1040

Lys  Gln  Leu  Glu  Ser  Glu  Gly  Arg  Ser  Pro  Ile  Phe  Thr  His  Leu  Val
                    1045                1050                1055

Thr  Ser  Leu  Lys  Gly  Leu  Trp  Thr  Leu  Arg  Ala  Phe  Gly  Arg  Gln  Pro
                    1060                1065                1070

Tyr  Phe  Glu  Thr  Leu  Phe  His  Lys  Ala  Leu  Asn  Leu  His  Thr  Ala  Asn
                    1075                1080                1085

Trp  Phe  Leu  Tyr  Leu  Ser  Thr  Leu  Arg  Trp  Phe  Gln  Met  Arg  Ile  Glu
                    1090                1095                1100

Met  Ile  Phe  Val  Ile  Phe  Phe  Ile  Ala  Val  Thr  Phe  Ile  Ser  Ile  Leu
1105                1110                1115                1120

Thr  Thr  Gly  Glu  Gly  Glu  Gly  Arg  Val  Gly  Ile  Ile  Leu  Thr  Leu  Ala
                    1125                1130                1135

Met  Asn  Ile  Met  Ser  Thr  Leu  Gln  Trp  Ala  Val  Asn  Ser  Ser  Ile  Asp
               1140                1145                1150

Val  Asp  Ser  Leu  Met  Arg  Ser  Val  Ser  Arg  Val  Phe  Lys  Phe  Ile  Asp
               1155                1160                1165

Met  Pro  Thr  Glu  Gly  Lys  Pro  Thr  Lys  Ser  Thr  Lys  Pro  Tyr  Lys  Asn
               1170                1175                1180

Gly  Gln  Leu  Ser  Lys  Val  Met  Ile  Ile  Glu  Asn  Ser  His  Val  Lys  Lys
1185                1190                1195                1200

Asp  Asp  Ile  Trp  Pro  Ser  Gly  Gly  Gln  Met  Thr  Val  Lys  Asp  Leu  Thr
                    1205                1210                1215

Ala  Lys  Tyr  Thr  Glu  Gly  Gly  Asn  Ala  Ile  Leu  Glu  Asn  Ile  Ser  Phe
               1220                1225                1230

Ser  Ile  Ser  Pro  Gly  Gln  Arg  Val  Gly  Leu  Leu  Gly  Arg  Thr  Gly  Ser
               1235                1240                1245

Gly  Lys  Ser  Thr  Leu  Leu  Ser  Ala  Phe  Leu  Arg  Leu  Leu  Asn  Thr  Glu
     1250                1255                1260

Gly  Glu  Ile  Gln  Ile  Asp  Gly  Val  Ser  Trp  Asp  Ser  Ile  Thr  Leu  Gln
1265                1270                1275                1280

Gln  Trp  Arg  Lys  Ala  Phe  Gly  Val  Ile  Pro  Gln  Lys  Val  Phe  Ile  Phe
               1285                1290                1295

Ser  Gly  Thr  Phe  Arg  Lys  Asn  Leu  Asp  Pro  Tyr  Glu  Gln  Trp  Ser  Asp
               1300                1305                1310

Gln  Glu  Ile  Trp  Lys  Val  Ala  Asp  Glu  Val  Gly  Leu  Arg  Ser  Val  Ile
               1315                1320                1325

Glu  Gln  Phe  Pro  Gly  Lys  Leu  Asp  Phe  Val  Leu  Val  Asp  Gly  Gly  Cys
               1330                1335                1340

Val  Leu  Ser  His  Gly  His  Lys  Gln  Leu  Met  Cys  Leu  Ala  Arg  Ser  Val
1345                1350                1355                1360

Leu  Ser  Lys  Ala  Lys  Ile  Leu  Leu  Leu  Asp  Glu  Pro  Ser  Ala  His  Leu
```

|   | 1365 | 1370 | 1375 |
|---|---|---|---|

Asp Pro Val Thr Tyr Gln Ile Ile Arg Arg Thr Leu Lys Gln Ala Phe
                1380                        1385                  1390

Ala Asp Cys Thr Val Ile Leu Cys Glu His Arg Ile Glu Ala Met Leu
           1395                    1400                 1405

Glu Cys Gln Gln Phe Leu Val Ile Glu Glu Asn Lys Val Arg Gln Tyr
    1410                  1415                  1420

Asp Ser Ile Gln Lys Leu Leu Asn Glu Arg Ser Leu Phe Arg Gln Ala
1425                1430                  1435              1440

Ile Ser Pro Ser Asp Arg Val Lys Leu Phe Pro His Arg Asn Ser Ser
             1445                  1450                1455

Lys Cys Lys Ser Lys Pro Gln Ile Ala Ala Leu Lys Glu Glu Thr Glu
            1460                  1465                1470

Glu Glu Val Gln Asp Thr Arg Leu
           1475                  1480

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GTTACATTCT GTTCT                                                                             15

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TCTGGAGATT TATGTTCTAT GGAATCTTTT TATAT                                      35

( 2 ) INFORMATION FOR SEQ ID NO:5:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GAGAAGGCTG TCCT                                                                              14

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

CTTGCTATGG GATTCT    16

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

ATACCACAGA AAGTATTT    18

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCTGCATTCC GTGCT    15

( 2 ) INFORMATION FOR SEQ ID NO:9:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GGNACANNNT GTTCT    15

DEOXYRIBONUCLEIC ACIDS CONTAINING INACTIVATED HORMONE RESPONSIVE ELEMENTS

RELATED APPLICATIONS

This application is related to the subject matter described in application U.S. Ser. No. 08/087,132, filed Jul. 2, 1993, which is a continuation application of U.S. Ser. No. 07/613,592, filed Nov. 15, 1990, which is in turn a continuation-in-part application of U.S. Ser. No. 07/539,295, filed Sep. 27, 1990, which is a continuation-in-part application of U.S. Ser. No. 07/488,307, filed Mar. 5, 1990. This application is also related to the subject matter described in application U.S. Ser. No. 08/130,682, filed Oct. 1, 1993, entitled "Gene Therapy for Cystic Fibrosis", which is a continuation-in-part application of U.S. Ser. No. 07/985,478, filed Dec. 2, 1992, and the subject matter described in application U.S. Ser. No. 08/088,416, filed Jul. 7, 1993, which is a continuation application of U.S. Ser. No. 07/770,204, filed Oct. 2, 1991. The contents of all of the above patent applications are incorporated herein by reference. Definitions of language or terms not provided in the present application are the same as those set forth in the applications. Any reagents or materials used in the examples of the present application whose source is not expressly identified also is the same as those described in the applications, e.g., ΔF508 CFTR gene and CFTR antibodies.

BACKGROUND OF THE INVENTION

Cystic Fibrosis (CF) is the most common fatal genetic disease in humans (Boat, T. F. et al. in The Metabolic Basis of Inherited Diseases (Scriver, C. R. et al. eds., McGraw-Hill, New York (1989)). Approximately one in every 2,500 infants in the U.S. is born with the disease. At the present time, there are approximately 30,000 CF patients in the U.S. Despite current standard therapy, the median age of survival is only 26 years. Disease of the pulmonary airways is the major cause of morbidity and is responsible for 95% of the mortality. The first manifestation of lung disease is often a cough, followed by progressive dyspnea. Tenacious sputum becomes purulent because of colonization of *Staphylococcus* and then with *Pseudomonas*. Chronic bronchitis and bronchiectasis can be partially treated with current therapy, but the course is punctuated by increasingly frequent exacerbations of the pulmonary disease. As the disease progresses, the patient's activity is progressively limited. End-stage lung disease is heralded by increasing hypoxemia, pulmonary hypertension, and cor pulmonale.

The upper airways of the nose and sinuses are also involved in CF. Most patients with CF develop chronic sinusitis. Nasal polyps occur in 15–20% of patients and are common by the second decade of life. Gastrointestinal problems are also frequent in CF; infants may suffer meconium ileus. Exocrine pancreatic insufficiency, which produces symptoms of malabsorption, is present in the large majority of patients with CF. Males are almost uniformly infertile and fertility is decreased in females.

Based on both genetic and molecular analyses, a gene associated with CF was isolated as part of 21 individual cDNA clones and its protein product predicted (Kerem, B. S. et al. (1989) *Science* 245:1073–1080; Riordan, J. R. et al. (1989) *Science* 245:1066–1073; Rommens, J. M. et al. (1989) *Science* 245:1059–1065)). U.S. Ser. No. 07/488,307 describes the construction of the gene into a continuous strand, expression of the gene as a functional protein and confirmation that mutations of the gene are responsible for CF. (See also Gregory, R. J. et al. (1990) *Nature* 347:382–386; Rich, D. P. et al. (1990) *Nature* 347:358–362). The co-pending patent application also discloses experiments which show that proteins expressed from wild type but not a mutant version of the cDNA complemented the defect in the cAMP regulated chloride channel shown previously to be characteristic of CF.

The protein product of the CF associated gene is called the cystic fibrosis transmembrane conductance regulator (CFTR) (Riordan, J. R. et al. (1989) *Science* 245:1066–1073). CFTR is a protein of approximately 1480 amino acids made up of two repeated elements, each comprising six transmembrane segments and a nucleotide binding domain. The two repeats are separated by a large, polar, so-called R-domain containing multiple potential phosphorylation sites. Based on its predicted domain structure, CFTR is a member of a class of related proteins which includes the multi-drug resistance (MDR) or P-glycoprotein, bovine adenyl cyclase, the yeast STE6 protein as well as several bacterial amino acid transport proteins (Riordan, J. R. et al. (1989) *Science* 245:1066–1073; Hyde, S. C. et al. (1990) *Nature* 346:362–365). Proteins in this group, characteristically, are involved in pumping molecules into or out of cells.

CFTR has been postulated to regulate the outward flow of anions from epithelial cells in response to phosphorylation by cyclic AMP-dependent protein kinase or protein kinase C (Riordan, J. R. et al. (1989) *Science* 245:1066–1073; Welsh, 1986; Frizzell, R. A. et al. (1986) *Science* 233:558–560; Welsh, M. J. and Liedtke, C. M. (1986) *Nature* 322:467; Li, M. et al. (1988) *Nature* 331:358–360; Hwang, T-C. et al. (1989) *Science* 244:1351–1353).

Sequence analysis of the CFTR gene has revealed a variety of mutations (Cutting, G. R. et al. (1990) *Nature* 346:366–369; Dean, M. et al. (1990) *Cell* 61:863–870; and Kerem, B-S. et al. (1989) *Science* 245:1073–1080; Kerem, B-S. et al. (1990) *Proc. Natl. Acad. Sci. U.S.A.* 87:8447–8451). Population studies have indicated that the most common CF mutation, a deletion of the 3 nucleotides that encode phenylalanine at position 508 of the CFTR amino acid sequence (ΔF508), is associated with approximately 70% of the cases of cystic fibrosis. This mutation results in the failure of an epithelial cell chloride channel to respond to cAMP (Frizzell R. A. et al. (1986) *Science* 233:558–560; Welsh, M. J. (1986) *Science* 232:1648–1650.; Li, M. et al. (1988) *Nature* 331:358–360; Quinton, P.M. (1989) *Clin. Chem.* 35:726–730). In airway cells, this leads to an imbalance in ion and fluid transport. It is widely believed that this causes abnormal mucus secretion, and ultimately results in pulmonary infection and epithelial cell damage.

Studies on the biosynthesis (Cheng, S. H. et al. (1990) *Cell* 63:827–834; Gregory, R. J. et al. (1991) *Mol. Cell Biol.* 11:3886–3893) and localization (Denning, G. M. et al. (1992) *J. Cell Biol.* 118:551–559) of CFTR ΔF508, as well as other CFTR mutants, indicate that many CFTR mutant proteins are not processed correctly and, as a result, are not delivered to the plasma membrane (Gregory, R. J. et al. (1991) *Mol. Cell Biol.* 11:3886–3893). These conclusions are consistent with earlier functional studies which failed to detect cAMP-stimulated Cl⁻ channels in cells expressing CFTR ΔF508 (Rich, D. P. et al. (1990) *Nature* 347:358–363; Anderson, M. P. et al. (1991) *Science* 251:679–682).

To date, the primary objectives of treatment for CF have been to control infection, promote mucus clearance, and improve nutrition (Boat, T. F. et al. in The Metabolic Basis of Inherited Diseases (Scriver, C. R. et al. eds., McGraw-Hill, New York (1989)). Intensive antibiotic use and a program of postural drainage with chest percussion are the mainstays of therapy. However, as the disease progresses, frequent hospitalizations are required. Nutritional regimens include pancreatic enzymes and fat-soluble vitamins. Bronchodilators are used at times. Corticosteroids have been used to reduce inflammation, but they may produce significant adverse effects and their benefits are not certain. In extreme cases, lung transplantation is sometimes attempted (Marshall, S. et al. (1990) *Chest* 98:1488).

Most efforts to develop new therapies for CF have focused on the pulmonary complications. Because CF mucus consists of a high concentration of DNA, derived from lysed neutrophils, one approach has been to develop recombinant human DNase (Shak, S. et al. (1990) *Proc. Natl. Sci. Acad U.S.A.* 87:9188). Preliminary reports suggest that aerosolized enzyme may be effective in reducing the viscosity of mucus. This could be helpful in clearing the airways of obstruction and perhaps in reducing infections. In an attempt to limit damage caused by an excess of neutrophil derived elastase, protease inhibitors have been tested. For example, α-1-antitrypsin purified from human plasma has been aerosolized to deliver enzyme activity to lungs of CF patients (McElvaney, N. et al. (1991) *The Lancet* 337:392). Another approach would be the use of agents to inhibit the action of oxidants derived from neutrophils. Although biochemical parameters have been successfully measured, the long term beneficial effects of these treatments have not been established.

Using a different rationale, other investigators have attempted to use pharmacological agents to reverse the abnormally decreased chloride secretion and increased sodium absorption in CF airways. Defective electrolyte transport by airway epithelia is thought to alter the composition of the respiratory secretions and mucus (Boat, T. F. et al. in The Metabolic Basis of Inherited Diseases (Striver, C. R. et al. eds., McGraw-Hill, New York (1989); Quinton, P. M. (1990) *FASEB J.* 4:2709–2717). Hence, pharmacological treatments aimed at correcting the abnormalities in electrolyte transport could be beneficial. Trials are in progress with aerosolized versions of the drug amiloride; amiloride is a diuretic that inhibits sodium channels, thereby inhibiting sodium absorption. Initial results indicate that the drug is safe and suggest a slight change in the rate of disease progression; as measured by lung function tests (Knowles, M. et al. (1990) *N. Eng. J. Med.* 322: 1189–1194; App, E. (1990) *Am. Rev. Respir. Dis.* 141:605). Nucleotides, such as ATP or UTP, stimulate purinergic receptors in the airway epithelium. As a result, they open a class of chloride channel that is different from CFTR chloride channels. In vitro studies indicate that ATP and UTP can stimulate chloride secretion (Knowles, M. et al. (1991) *N. Eng. J. Med* 325:533). Preliminary trials to test the ability of nucleotides to stimulate secretion in vivo, and thereby correct the electrolyte transport abnormalities are underway.

Despite progress in therapy, cystic fibrosis remains a lethal disease, and no current therapy treats the basic defect. However, two general approaches may prove feasible. These are: 1) protein replacement therapy to deliver the wild type protein to patients to augment their defective protein, and; 2) gene replacement therapy to deliver wild type copies of the CF associated gene. Since the most life threatening manifestations of CF involve pulmonary complications, epithelial cells of the upper airways are appropriate target cells for therapy.

The feasibility of gene therapy has been established by introducing a wild type cDNA into epithelial cells from a CF patient and demonstrating complementation of the hallmark defect in chloride ion transport (Rich, D. P. et al. (1990) *Nature* 347:358–363).

SUMMARY OF THE INVENTION

The present invention is based, at least in part, on the discovery that overexpression of CFTR in cultured cells can lead to growth arrest at the G2/M boundary and in selective lethality in male transgenic rabbits. Male transgenic rabbit lethality is the result of activation of steroid hormone responsive elements in the CFTR cDNA. The steroid hormone responsive elements are activated during fetal development of the male transgenic rabbits. Activated hormone responsive elements stimulate transcription of the CFTR cDNA. Thus, CFTR expression is augmented inappropriately in certain tissues during fetal development of male rabbits which ultimately leads to death. The activation of the responsive elements can be by circulating steroids, e.g., androgens. Inactivation of the steroid hormone responsive elements in the CFTR cDNA provides a solution to this problem.

The present invention pertains to DNA which comprises at least one inactivated hormone responsive element, such as an androgen responsive element, and a nucleic acid sequence which encodes a membrane-associated protein, such as an ion channel. In one embodiment of the invention, the membrane-associated protein is CFTR and the androgen responsive element is a sequence in the coding region of CFTR which is inactivated in at least one species in which it was formerly functional. Other aspects of the present invention include cells, such as cystic fibrosis (CF)-affected cells, mammalian embryos, and mammals which comprise the above-described DNA.

The present invention further pertains to therapeutic compositions for treating a subject having CF. The therapeutic composition includes a therapeutically effective amount of a DNA comprising at least one inactivated hormone responsive element and a nucleic acid sequence encoding CFTR and a pharmaceutically acceptable carrier.

The instant invention still further pertains to methods of treating a subject having CF. The method includes providing a DNA comprising at least one inactivated hormone responsive element and a nucleic acid sequence encoding CFTR and administering to a subject having CF an effective amount of the DNA such that functional CFTR is produced by the subject at a level which is not detrimental to the subject.

Another aspect of the present invention is a method of introducing DNA into a cell. The method comprises selecting a DNA comprising a nucleic acid sequence encoding a membrane-associated protein, introducing the DNA into the cell, and expressing the membrane-associated protein at a level which is not detrimental to the cell. The present invention also pertains to cells produced by this method. Yet another aspect of the present invention is a CF-affected cell which produces CFTR at a level which is not detrimental to the cell.

Still another aspect of the present invention is a method of assaying DNA for the presence or absence of a hormone responsive element in a species in which the hormone responsive element is functional. The method includes introducing into mammalian embryos a DNA, determining the effect of the DNA on the mortality of male and female mammals developed from the mammalian embryos, and correlating the effect on the mortality to the presence or absence of DNA comprising a nucleic acid sequence having a hormone responsive element.

The present invention also pertains to a method of selectively breeding female transgenic mammals which produce a protein of interest. The method includes introducing into a mammalian embryo a DNA comprising at least one androgen responsive element and a nucleic acid sequence encoding a protein of interest, implanting the embryo into a pregnant female mammal, and allowing the implanted embryo to undergo gestation such that the female transgenic mammals are viable at birth and the male transgenic mammals are not viable at birth due to the detrimental effect of the androgen responsive element.

BRIEF DESCRIPTION OF THE DRAWINGS

FIG. 12 shows a table depicting data which demonstrate that expression of wild type CFTR is non-lethal in female transgenic rabbits and lethal in male transgenic rabbits. The table also presents data which demonstrate that expression of a nonglycosylated variant of CFTR is non-lethal in female transgenic rabbits and lethal in male transgenic rabbits but at a reduced potency. The selective lethality observed in male rabbits was also manifest in the F1 generation but at a lower penetrance;

FIG. 13 is a table demonstrating viability of transgenic rabbits containing G551D-CFTR. The G551D mutation results in the synthesis of a variant that is post-translationally processed and delivered to the plasma membrane but whose Cl⁻ channel activity is severely defective. No lethality was observed in the founder animals bearing the G551D-CFTR transgene. Therefore, the male lethality observed in transgenic rabbits most likely a consequence of the Cl⁻ channel activity of wild type CFTR; and FIG. 14 shows an exemplary consensus sequence from the nucleic acid encoding human CFTR which corresponds to an androgen responsive element.

DETAILED DESCRIPTION OF THE INVENTION

Figure 1:
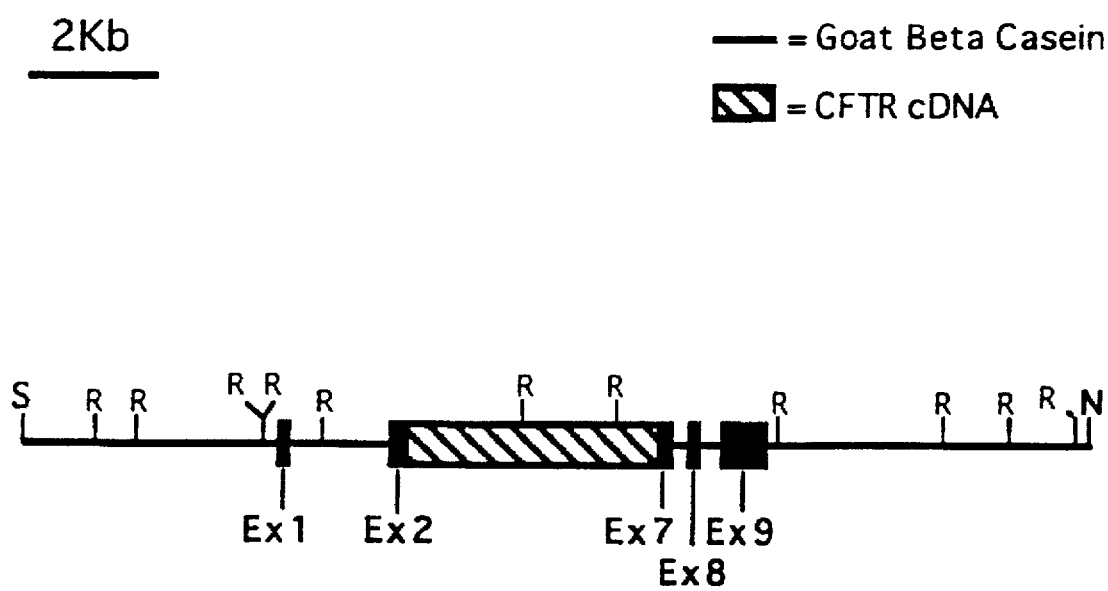
FIG. 1 depicts the structure of the mammary specific expression vector. Abbreviations: S, SalI; R, EcoRI; N NotI.

The present invention pertains to DNA which comprises at least one inactivated hormone responsive element, such as an androgen responsive element, and a nucleic acid sequence which encodes a membrane-associated protein, such as an ion channel. In one embodiment of the invention, the membrane-associated protein is CFTR and the androgen responsive element is a sequence in the coding region of CFTR which is inactivated in at least one species in which it was formerly functional. Other aspects of the present invention include cells, such as cystic fibrosis (CF)-affected cells, mammalian embryos, and mammals which comprise the above-described DNA.

The term "DNA" refers to deoxyribonucleic acid which is an art-recognized term. DNA is intended to include single- or double-stranded genomic or copy DNA (cDNA). The DNA can be in the form naked DNA, a plasmid, or enclosed in a virus.

The language "membrane-associated protein" is intended to include transmembrane proteins, peripheral membrane proteins, and integral membrane proteins. Examples of membrane-associated proteins include receptors, such as membrane steroid hormone receptors, viral glycoproteins, and transporters. Other examples of a membrane-associated proteins include ion channels, particularly chloride ion channels such as CFTR (the nucleic acid sequence which encodes CFTR is shown as SEQ ID NO:1 (this sequence corresponds to the sequence shown in Gregory, R. J. et al. (1990) Nature 347:382–386); the amino acid sequence of CFTR is shown as SEQ ID NO:2), which, when introduced into a CF-affected cell, lessen or alleviate symptoms of CF and/or generate functional ion channels or mediate ion transport. Transmembrane proteins extend across the membrane. Peripheral membrane proteins are bound to one or the other face of the membrane generally through interactions with, for example, other membrane-associated proteins. Peripheral membrane proteins can also be associated with the membrane by attachment to a fatty acid chain inserted into the membrane or by attachment to an oligosaccharide which is in turn attached to a fatty acid chain inserted into the membrane. Integral membrane proteins are generally transmembrane proteins linked to a fatty acid chain in the membrane.

The term "membrane" is intended to include lipid membranes normally found in cells and with which a membrane-associated protein is normally associated. For example, CFTR is normally located within the plasma membrane of a cell. However, other membrane-associated proteins of the present invention are normally associated with the membrane of the endoplasmic reticulum, the membrane of the Golgi apparatus, or a membrane enclosing a different cellular organelle.

The language "hormone responsive element" is art-recognized and is intended to include regions of DNA which, prior to inactivation, regulate transcription of genes in response to hormone activation in at least one species. Hormone responsive elements are typically about 10 to about 40 nucleotides in length, more typically about 13 to 20 nucleotides in length, and can be activated when a particular hormone, such as asteroid hormone, binds to its intracellular receptor causing a conformational change in the receptor that increases the receptor's affinity for the hormone responsive element and enables it to bind to the hormone responsive element. Receptor-binding to the hormone responsive element then stimulates (or in some cases suppresses) transcription of various genes. It is also known that steroid hormone receptors can be present on the plasma membrane of a cell. The hormone responsive elements of the present invention can be activated by steroid hormones, particularly androgens such as testosterone and androsterone. Alternatively, the hormone responsive elements can be activated by glucocorticoids or metabolic products of estrogens. Examples of hormone responsive element consensus sequences present in the DNA encoding CFTR include nucleotides 2988 to 3002 (5' GTTACATTCTGTTCT 3') (SEQ ID NO:3) (See et al. (1992) Mol. Endocrinol. 6:2229–2235), nucleotides 365 to 399 (5' TCTGGAGATT-TATGTTCTATGGAATCTTTTTATAT 3') (SEQ ID NO:4), (Claessens, F. et al. (1990) Mol. Cell Endocrinol. 74:203–212), nucleotides 2331 to 2344 (5' GAGAAGGCT-GTCCT 3') (SEQ ID NO:5), nucleotides 2911 to 2926 (5' CTTGCTATGGGATTCT 3') (SEQ ID NO:6), nucleotides 3997 to 4014 (5' ATACCACAGAAAGTATTT 3') (SEQ ID NO:7). The hormone responsive elements, particularly hormone responsive elements that are activated by male- or female-specific hormones, of the present invention can be operably linked to nucleic acid sequences encoding a male- or female specific protein in order to study the effects of expression of a male- or female-specific protein in the reproductive organs of the opposite sex. For example, an androgen responsive element can be operably linked to the gene encoding uteroglobin, a protein expressed in female reproductive tissues, such as the uterus. Such a construct can be introduced into a mammalian embryo and the embryo reimplanted into a pregnant female. The effects on the male reproductive organs of male transgenic mammals developed from such embryos can then be studied.

The term "inactivated" is intended to include rendering a hormone responsive element, which is functional in at least one species, nonfunctional. Inactivation of a hormone responsive element can be brought about by, for example, alteration, through nucleotide addition, deletion, or substitution, of the nucleotide sequence of the hormone responsive element. However, if the hormone responsive element is located within the coding sequence of the membrane-associated protein, inactivation of the hormone responsive element should not significantly interfere with the normal localization and function of the membrane-associated protein. Inactivation by alteration of the nucleotide sequence of the hormone responsive element can, but need not, result in a corresponding amino acid alteration in the amino acid sequence of the membrane-associated protein. If the alteration of the nucleotide sequence does result in an altered amino acid sequence, the amino acid alteration should not significantly interfere with the normal function and localization of the membrane-associated protein. Methods of altering a hormone responsive element by nucleotide deletion, addition, or substitution, such as by oligonucleotide-mediated mutagenesis, are well known and commonly employed by those of ordinary skill in the art. Sambrook, J. et al. Molecular Cloning: A Laboratory Manual (Cold Spring Harbor Laboratory Press 1989).

The language "cystic fibrosis-affected cell" is intended to include a cell associated with cystic fibrosis (CF) which, as it exists in nature, contains CFTR, in its normal or mutant form; or a cell which, as it exists in nature, does not contain CFTR, in its normal and mutant form, but is engineered to express CFTR, in its normal or mutant form. Examples of cells that contain CFTR as they exist in nature include airway epithelial cells such as nasal and lung epithelia of CF victims. Examples of cells which do not normally contain mutant CFTR but can be engineered to express mutant CFTR include BTS cells, one-celled mammalian embryos, 3T3 fibroblasts, C127, and COS-7 cells. These cells can be transfected with nucleic acid which encodes and directs expression of mutant CFTR, such as CFTRΔF508. See Example 15 of U.S. Ser. No. 935,603, filed Aug. 26, 1992. It should be understood that the present methods of introducing DNA into a cystic fibrosis-affected cell also can be used to transfer DNA into cells which are not considered to be cystic fibrosis-affected. The cell can be any cell capable of providing a desired effect from the introduction of the DNA of the present invention.

The term "embryo" is intended to include fertilized embryos comprising at least one cell. The term "mammal" is art-recognized and is intended to include an animal of the class Mammalia. Examples of mammals include humans, dogs, cats, horses, cows, goats, rats, and mice.

The present invention also pertains to a therapeutic composition for treating a subject having cystic fibrosis. The therapeutic composition includes a therapeutically effective amount of a DNA comprising at least one inactivated hormone responsive element and a nucleic acid sequence encoding cystic fibrosis transmembrane conductance regulator and a pharmaceutically acceptable carrier.

The term "subject" is intended to include living organisms susceptible to CF, e.g., mammals. Examples of subjects include humans, dogs, cats, horses, cows, goats, rats and mice. The term subject further is intended to include transgenic species.

Cystic fibrosis (CF) is a well-known disease state. (See, e.g., Boat, T. et al. Cystic fibrosis. In: *The Metabolic Basis of Inherited Disease*, C. Scriver, A. Beaudet, W. Sly, and D. Valle, eds. (McGraw Hill, New York, 1989) 2649–2860) CF is a disease of infants, children, adolescents, and young adults involving the exocrine glands, especially those secreting mucus. Symptoms associated with CF are many and varied and include, for example, pancreatic insufficiency, chronic pulmonary disease, abnormally high sweat electrolyte levels, and, in some cases, cirrhosis of the liver.

The language "therapeutically effective amount" is intended to include that amount sufficient or necessary to significantly reduce or eliminate a subject's symptoms associated with CF. The amount can be determined based on such factors as the type and severity of symptoms being treated, the weight and/or age of the subject, the previous medical history of the subject, and the selected route for administration of the DNA. The determination of appropriate "effective amounts" is within the ordinary skill of the art.

The language "pharmaceutically acceptable carrier" is intended to include substances capable of being co-administered with the DNA and which allow the DNA to perform its intended function, e.g. allowing expression of a membrane-associated protein, such as CFTR, at a level which is not detrimental to the subject. Examples of such carriers include solvents, dispersion media, delay agents and the like. The use of such media and agents for pharmaceutically active substances is well known in the art. Any conventional media and agent compatible with the DNA can be used with this invention. The DNA of this invention can be administered alone or in a pharmaceutically accepted carrier.

The present invention further pertains to a method of treating a subject having CF by providing a DNA comprising at least one inactivated hormone responsive element and a nucleic acid sequence encoding cystic fibrosis transmembrane conductance regulator and administering to a subject having cystic fibrosis an effective amount of the DNA. The DNA is administered such that functional cystic fibrosis transmembrane conductance regulator is produced by the subject at a level which is not detrimental to the subject.

The DNA of the present invention can be administered to a subject through a route of administration which allows the DNA to perform its intended function, e.g. allowing expression of a membrane-associated protein, such as CFTR, at a level which is not detrimental to the subject. Examples of routes of administration which can be used include injection (subcutaneous, intravenous, parenteral, intraperitoneal, etc.), enteral, transdermal, and rectal. A route of administration that is particularly useful for treatment of CF is through the respiratory system, e.g., by nasal, intratracheal, or intrapulmonary instillation of the DNA or inhalation of an aerosolized solution containing the DNA. Depending on the route of administration, the DNA can be coated with or in a material to protect it from the natural conditions which may detrimentally affect its ability to perform its intended function. The administration of the DNA is done at dosages and for periods of time effective to significantly reduce or eliminate the symptoms associated with CF. Dosage regimes may be adjusted for purposes of improving the therapeutic response of the DNA. For example, several divided doses may be administered daily or the dose may be proportionally reduced as indicated by the exigencies of the therapeutic situation.

The term "produced" is intended to include expression of CFTR in cells of the subject. The language "a level which is not detrimental to the subject" is intended to include an amount of CFTR which does not significantly interfere with normal bodily functions of the subject. Preferably, the CFTR is produced at a level which is beneficial to a subject having cystic fibrosis, e.g., it lessens symptoms associated with CF.

The present invention still further pertains to a method of introducing DNA into a cell. The method includes selecting a DNA comprising a nucleic acid sequence encoding a membrane-associated protein, introducing the DNA into the cell, and producing the membrane-associated protein at a level which is not detrimental to the cell. In one embodiment, the membrane-associated protein is CFTR and the cell is a CF-affected cell.

The term "introducing" is intended to include insertion of DNA into a cell. Several methods of inserting DNA into cells are well known and commonly practiced by those of ordinary skill in the art. Examples of well known methods of inserting DNA into a cell include calcium phosphate-mediated DNA transfection, electroporation, microinjection of the DNA into a cell, for example, into a mammalian embryo in order to generate a transgenic mammal, and virus-mediated delivery of the DNA to a cell, e.g. using retrovital vectors or adenovirus-based vectors. See, e.g., U.S. Ser. No. 07/985,478, filed Dec. 2, 1992.

The language "at a level which is not detrimental to the cell" is intended to include an amount of CFTR which does not significantly interfere with normal functions of the cell. Interference of normal cellular functions include, for example, production of a membrane-associated protein at a level which decreases or increases the rate or number of normal cellular processes in a manner that is toxic to the cell. For example, ion channels can be overexpressed to a level such that normal intracellular ion gradients are disrupted, resulting in an abnormal influx or efflux of the ion for which the channel is specific. An abnormal influx of an ion, such as calcium or chloride, can be toxic to a cell.

Another aspect of the present invention is a method of assaying DNA for the presence or absence of a hormone responsive element in a species in which the hormone responsive element is functional. The method includes introducing into mammalian embryos a DNA, determining the effect of the DNA on the mortality of male and female mammals developed from the mammalian embryos, and correlating the effect on the mortality to the presence or absence of DNA comprising a nucleic acid sequence having a hormone responsive element.

The language "determining the effect of the DNA on the mortality of male and female mammals developed from the mammalian embryos" is intended to include ascertaining whether male or female or both male and female transgenic mammals which develop from the genetically manipulated mammalian embryos are born viable or non-viable. If the mammal is born viable but dies soon after birth, it is considered non-viable at birth for purposes of the present invention.

The language "correlating the effect on the mortality to the presence or absence of DNA comprising a nucleic acid sequence having a hormone responsive element" is intended to include relating the death of one sex of mammals developed from the embryos to the presence of a hormone responsive element in the DNA that is activated (or suppressed) by a hormone present predominantly in females or males, relating the death of both sexes to the presence of a hormone responsive element that is activated (or suppressed) by a hormone present in both males and females, or relating the viability of both sexes to the absence of a hormone responsive element in the DNA.

Yet another aspect of the present invention is a method of selectively breeding female transgenic mammals which produce a protein of interest. The method includes introducing into a mammalian embryo a DNA comprising at least one androgen responsive element and a nucleic acid sequence encoding a protein of interest; implanting the embryo into a pregnant female mammal; and allowing the implanted embryo to undergo gestation such that the female transgenic mammals are viable at birth and the male transgenic mammals are not viable at birth due to the detrimental effect of the androgen responsive element.

The language "transgenic mammal" is intended to include a mammal whose cells, e.g., germline or somatic, have been genetically manipulated such that foreign DNA segments have been introduced therein. Examples of transgenic mammals include transgenic cows, sheep, goats (Ebert, K. et al. (1991) Bio/Technology 9:835), pigs, rabbits, rats, and mice (DiTullio, P. et al. (1999) Bio/Technology 10:74; Gordon, K. et al. (1987) Bio/Technology 5:1183).

The language "protein of interest" is intended to include proteins that a person desires to study or to produce commercially. Proteins of interest can be produced by a transgenic mammal, preferably in the milk of a transgenic female mammal. Examples of proteins of interest include human pharmaceuticals. Examples of such pharmaceuticals include insulin, longer-acting tissue-type plasminogen activator, anti-thrombin III, α-1-anti-trypsin, soluble CD4, interleukin-2, immunoglobulins, CFTR, and coagulation factors VIII and IX.

The language "detrimental effect of the androgen responsive element" is intended to include androgen-mediated male selective toxicity. For example, the introduced DNA can contain transcriptional enhancer-type elements which are activated by male-specific hormones only such that they mediate over- or underexpression of a gene. Over- or underexpression of the gene is then toxic only to male embryos.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example 1

Generation of DNA Constructs

Generation of Constructs Containing Glycosylated CFTR

The 17.8 kb DNA construct used to produce transgenic rabbits capable of secreting CFTR in their milk is shown in FIG. 1. It consists of a full length copy of CFTR cDNA containing a point mutation at residue 936 to inactivate an internal cryptic bacterial promoter that otherwise renders the cDNA unstable (Cheng, S. H. et al. (1991 ) Cell 66:1027–1036) inserted between exons 2 and 7 of the goat β-casein gene. The β-casein gene contains a mammary gland specific promoter which results in expression of the desired gene, e.g., CFTR or other membrane-associated protein, within the mammary gland. Other milk specific promoters which may be used in substitution include well known promoters such as α-casein, whey acid protein, and β-lactoglobulin promoters.

Most preferred constructs will include one or more enhancer elements typically associated with such genes as have been described previously in the art. Such promoters/ enhancers are then associated with the coding sequence of the membrane-associated protein of interest using conventional recombinant techniques. Such coding sequences may be either cDNA, partial or fully genomic DNA but more preferably, either of the latter two categories since such have been shown in transgenic systems to cause greater levels of expression. More particularly, the 4.5 kb SalI-SalI fragment from pMT-CFTR (Cheng, S. H. et al. (1990) Science 253:202–205) was cloned into the Xho I site of CAS 1441. The cosmid vector CAS 1441 contains an altered goat β-casein gene with an Xho I site in place of the coding portion of the gene. Earlier studies have characterized the goat casein gene and shown that it directs the synthesis of a number of gene products in the milk of both transgenic mice and goats in a tissue-specific manner. Denman, J. et al. (1991) Bio/Technology 9:835–838; Ebert, K. M. et al. (1991) Bio/Technology 9:839–843 The portion deleted extends from the Taq I site in exon 2 to the PpuM I site in exon 7.

With reference to FIG. 2, a goat genomic DNA library was constructed by cloning DNA fragments generated by partial MboI digestion of Saanen goat DNA into EMBL3 phage as described by Maniatis, T. et al. Molecular Cloning: A Laboratory Manual (Cold Spring Harbor Laboratory Press, New York 1982). The library, consisting of a $1.2 \times 10^6$ recombinant phage, was screened with a 1.5 kb HindIII/ TthIII1 DNA fragment encoding the entire mouse beta casein cDNA as described by Maniatis, T. et al. Molecular Cloning: A Laboratory Manual (Cold Spring Harbor Laboratory Press, New York 1982). Three plaques designated 3-7, 3-8, and 3-11 exhibited the strongest hybridization signals under conditions of high stringency and each were subjected to three rounds of plaque purification. Restriction enzyme and Southern blotting analysis revealed that the inserts within recombinant phage 3-7 and 3-8 were subfragments of the 18.5 kb insert contained in phage 3-11. Therefore, all DNA fragments used for construction of a mammary gland specific expression vector were derived from clone 3-11 which is shown in FIG. 2A. All subclones were constructed in pUC or pUC derivatives with modified polylinker To construct a mammary gland specific expression vector, the entire upstream (5' portion) region from the SalI site to exon 2 and the entire downstream (3' portion) region from exon 7 to the SalI site of the goat beta casein gene was used to direct expression to the mammary gland. To engineer the 5' end of the β-casein gene, the TaqI site in exon 2 of clone Bc106 was replaced with a BamHI restriction site to produce the plasmid Bc150 (FIG. 2A). The entire available 5' region of the goat β-casein gene was constructed by the sequential addition of the subclones Bc104, Bc147, and Bc103 (FIG. 2A). The orientation of subclone Bc147 was verified by restriction analysis. The final vector designated Bc113 contains a SalI site at the 5' end and a BamHI site at the 3' end. The downstream BamHI was subsequently changed to an XhoI site to form Bc114.

The 3' end of the goat β-casein gene was constructed in a similar fashion to the 5' end. The 1.8 kb Bc108 clone (FIG. 2A) was digested with PpuMI to allow for the addition of a BamHI linker. The BamHI/HindIII fragment from the engineered clone Bc108 was ligated into the vector Bc109 which contained the extreme 3' flanking region of the goat β-casein gene. The entire 3' end was completed by the addition of 4.4 kb HindIII fragment from Bc108 was cloned into the modified Bc109 vector and screened for orientation. The new vector was designated Bc118 and contained the entire 3' region of beta casein from exon 7 through the poly A signal and 5 kb downstream to the SalI site of EMBL clone 3-11. Subsequently, an XhoI site was introduced at the 5' BamHI site and a NotI site at the 3' SalI site of Bc118 to produce the vector Bc122.

Figure 2A:
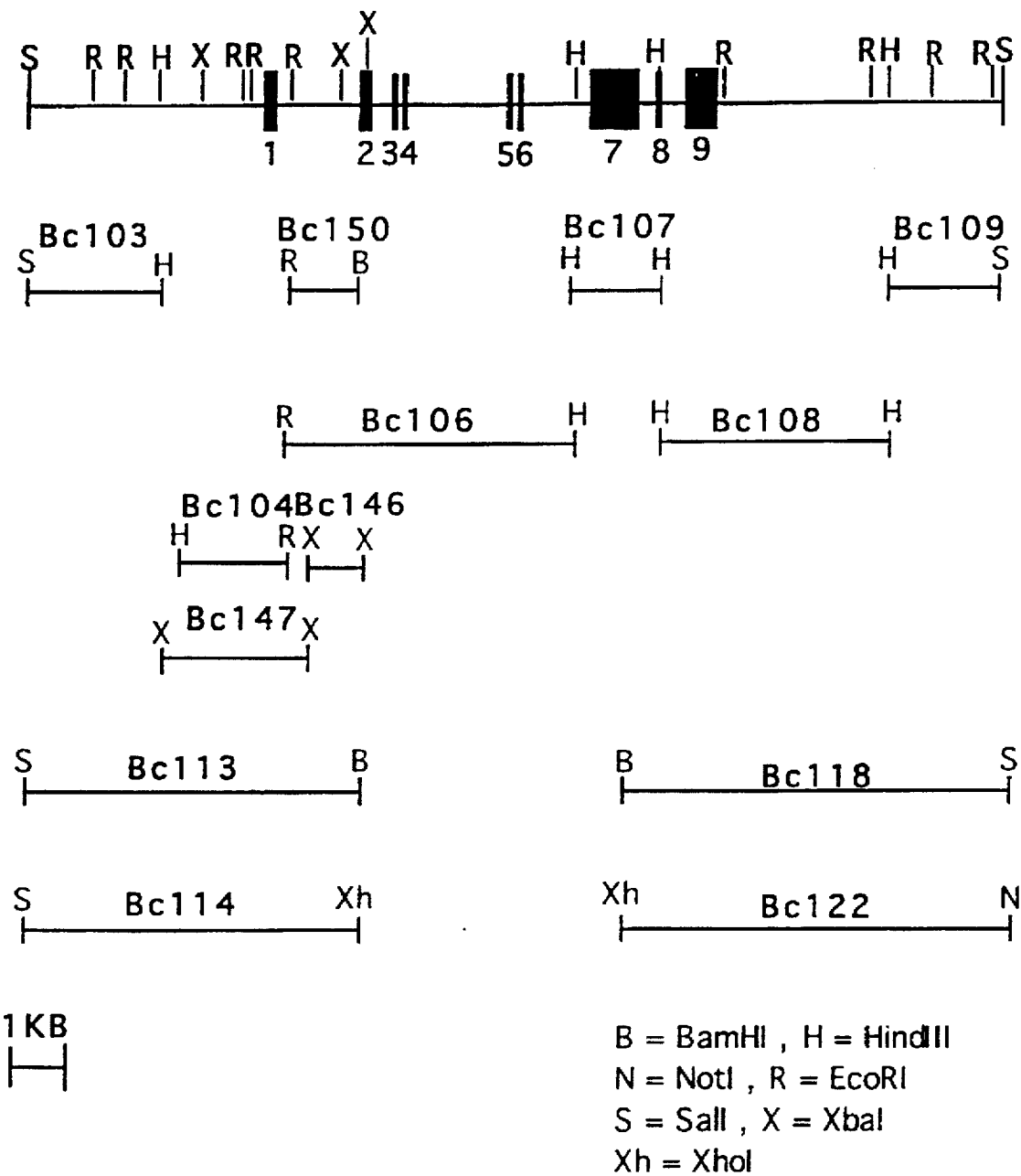
FIGS. 2A–2C graphically depict vector constructs containing CFTR cDNA for introduction into BTS cells and rabbit embryos.
Figure 2B:
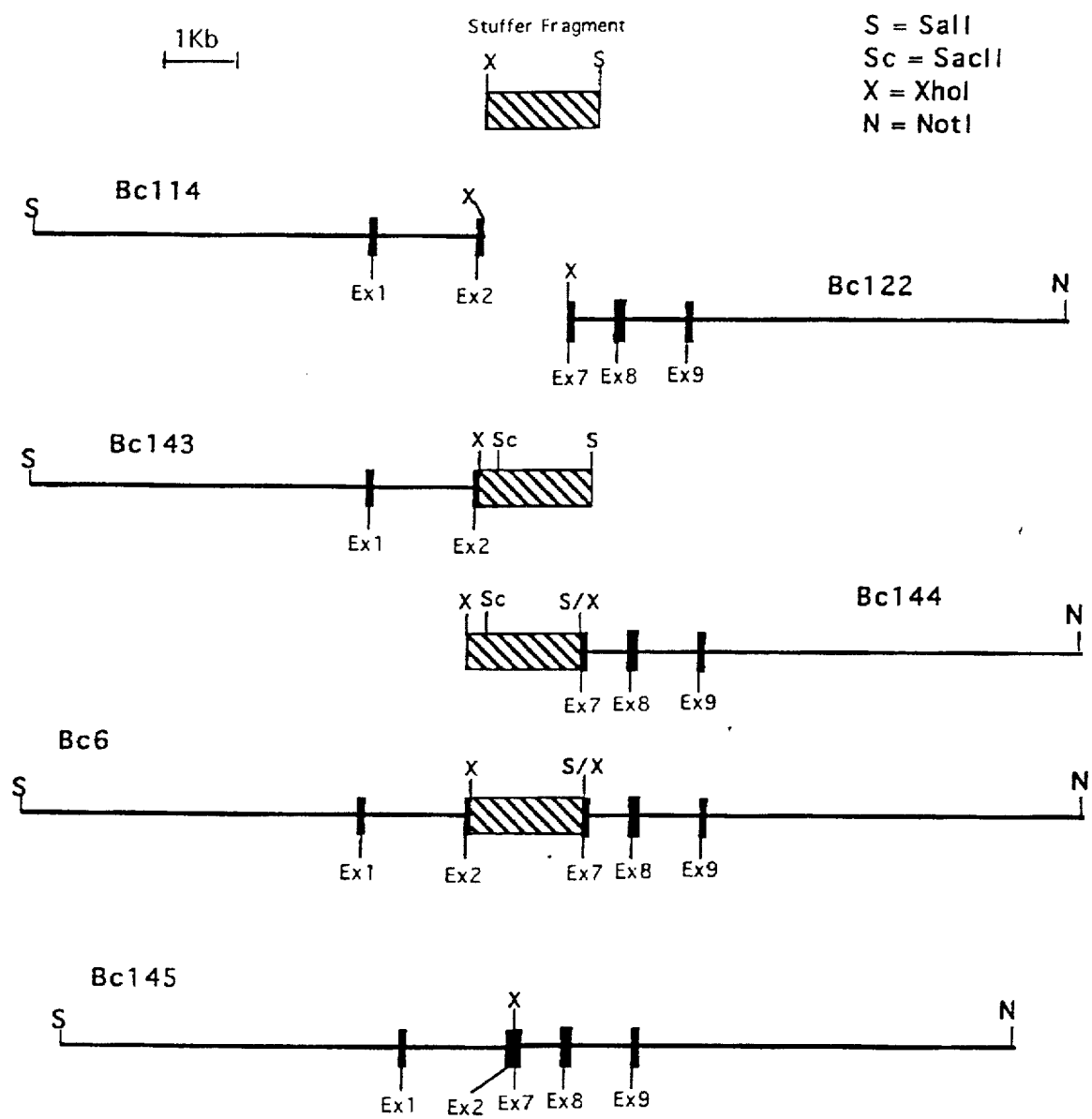
Figure 2C:
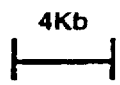
Figure 2C:
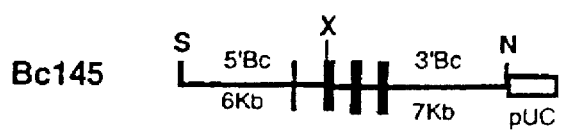
Figure 2C:
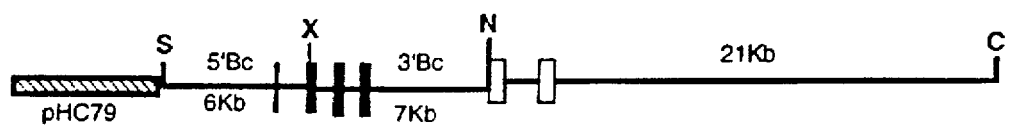
Figure 2C:
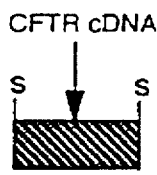
Figure 2C:
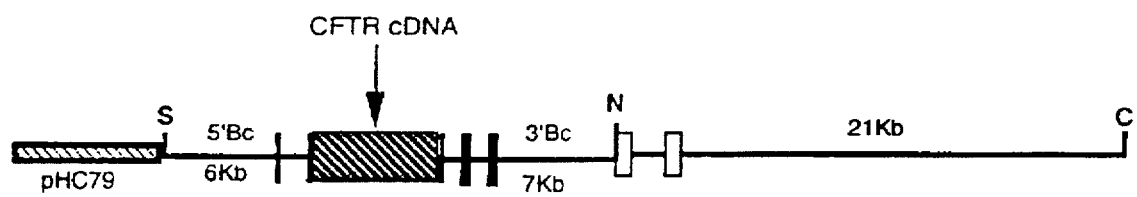
Figure 2C:
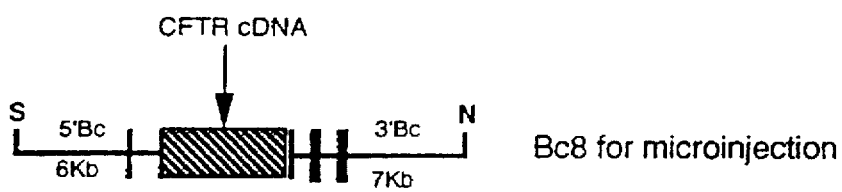

The overall cloning strategy followed to construct the beta casein CFTR vector (Bc8) is shown in FIG. 2B and 2C. To construct a goat β-casein vector containing all the available upstream and downstream sequences, a 1.7 kb XhoI to SalI stuffer fragment containing a unique SacII site was cloned into the XhoI site of Bc114 and Bc122 to form vectors Bc143 and Bc144, respectively. The complete vector was made by cloning the SalI to SacII fragment from Bc143 into a SalI to SacII cut Bc144 to form the plasmid Bc6. The stuffer fragment was removed from the plasmid by digestion with BamHI and a unique XhoI site was inserted to form the vector Bc145. The SalI to NotI fragment from Bc145 which contains the 5' and 3' β-casein sequences was subcloned into the cosmid clone CAS1438 to form the cosmid CAS 1441. CAS 1438 is a cosmid vector constructed in pHC79 containing an engineered SalI and NotI site and 21 kb or 5' flanking sequence from the Bovine α-casein gene (Meade, H. et al. Biotechnology 8, 443–445 1990). The expression vector Bc8 was constructed by digesting the vector CAS1441 with XhoI and ligating in the 4.5 kb SalI fragment from pMT-CFTR. Gregory, R. J. et al. (1991) *Mol. Cell Biol.* 11: 3886–3893; Gregory, R. J. et al. (1990) *Nature* 347:382–386. Orientation of the CFTR cDNA was confirmed by restriction analysis. To obtain a fragment for microinjection, the vector Bc8 was digested with SalI and NotI to release the beta casein CFTR portion of the vector for purification. The final microinjection fragment contained 4.2 kb of 5' flanking sequence, exon 1, intron 1, a portion of exon 2, 4.5 kb CFTR cDNA, a portion of exon 7, intron 7, exon 8, intron 8, exon 9, and 5.3 kb of 3' flanking sequence.

Generation of Constructs Containing Nonglycosylated and Non-functional Mutant CFTR To construct mammary gland expression vectors for the production of the nonglycosylated and non-functional mutants of CFTR, the β-casein cloning vector was modified and cloned into a smaller cosmid vector to facilitate isolation of the microinjection fragment. The 5' SalI site of CAS 1441 was converted to a NotI site to form the vector CAS1457. The vector CAS1457 was digested with NotI to isolate the goat β-casein promoter with 3' flanking region which were cloned into the cosmid Supercos (Stratagene, LaJolla, Calif.). The new β-casein cloning vector was designated Bc157.

Bc157 was digested with XhoI and the Sail fragment from pMT-N894, 900Q was cloned into the XhoI site. Orientation of the cDNA was checked by restriction analysis and DNA sequencing. This new mammary gland expression vector was used to direct expression of the nonglycosylated mutant of CFTR to the milk of transgenic rabbits and was designated Bc36. The Bc36 vector was digested with NotI to remove all bacterial sequences and the fragment prepared for microinjection. The non-functional CFTR mutant was isolated as a SalI fragment from the plasmid pMT-G551D and cloned into the XhoI site of Bc157. The new expression vector was designated Bc59 and orientation was analyzed by restriction analysis. The β-casein CFTR transgene was excised from the Bc59 vector by digestion with NotI and prepared for microinjection.

Example 2

Expression Systems

First Expression System: BTS Cells

Figure 3:
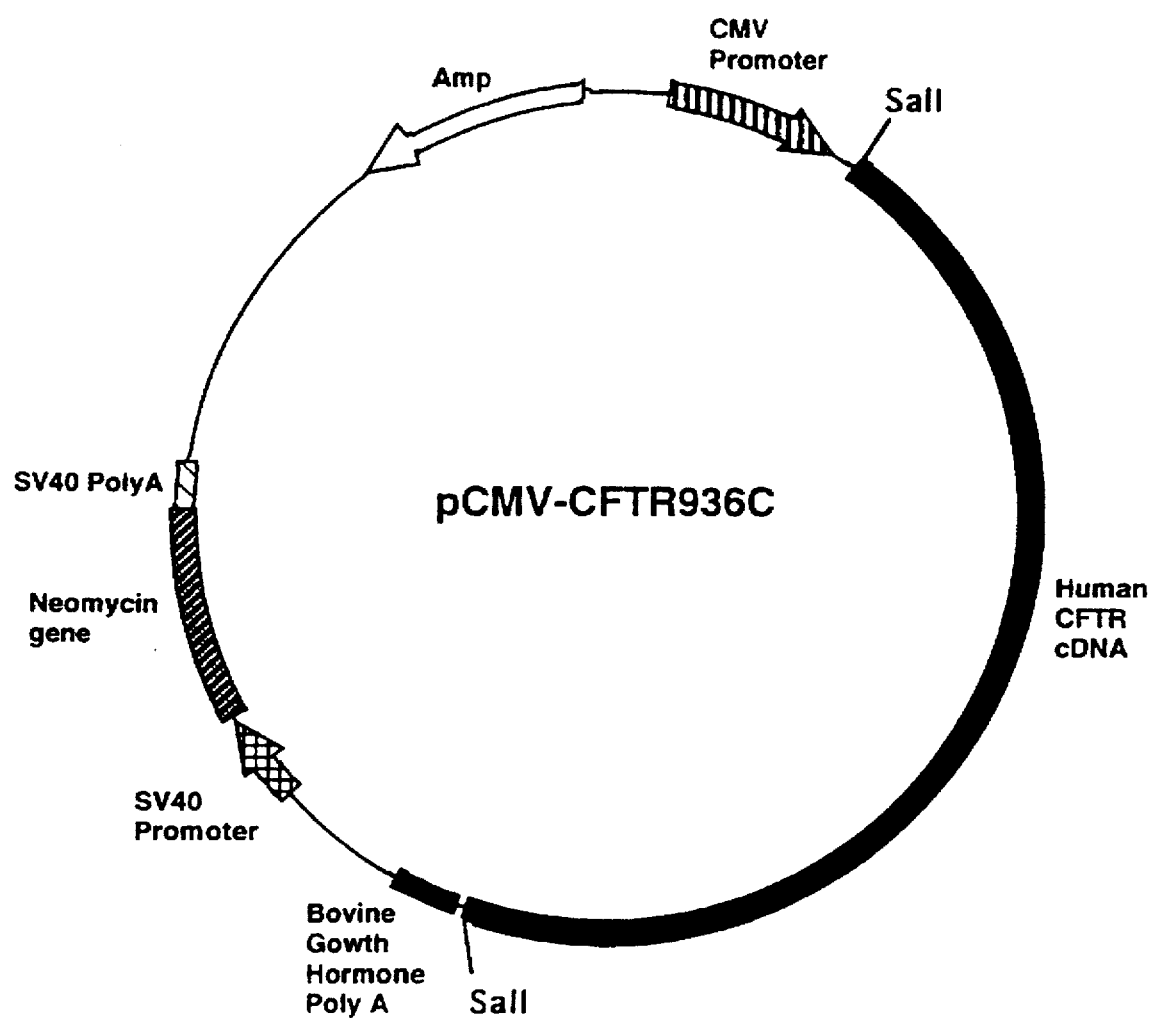
FIG. 3 is a map of pCMV-CFTR-936c which was the plasmid used to transfect BTS cells.
Figure 4:
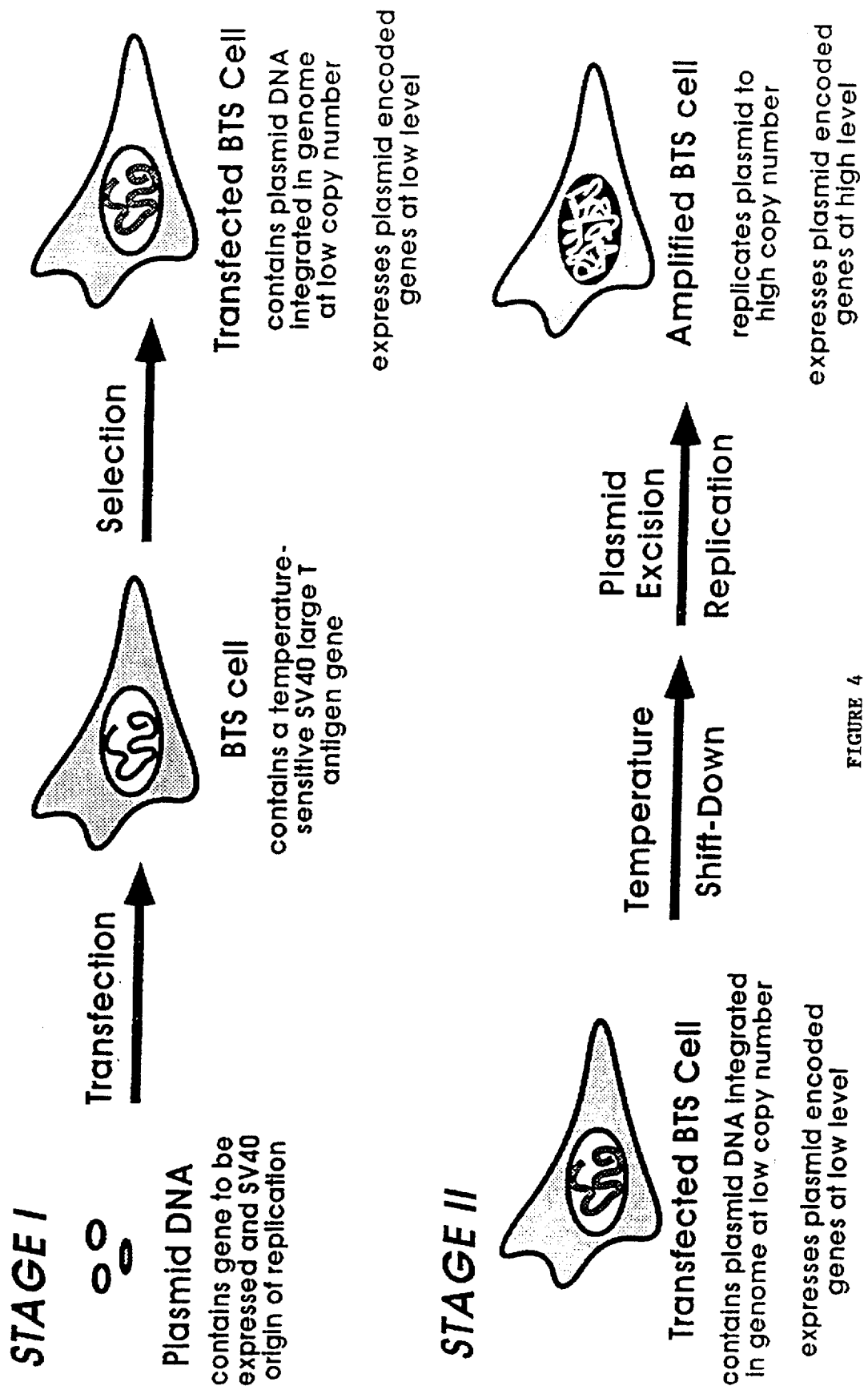
FIG. 4 is a schematic of the BTS cell system used to overexpress CFTR.
Figure 5:
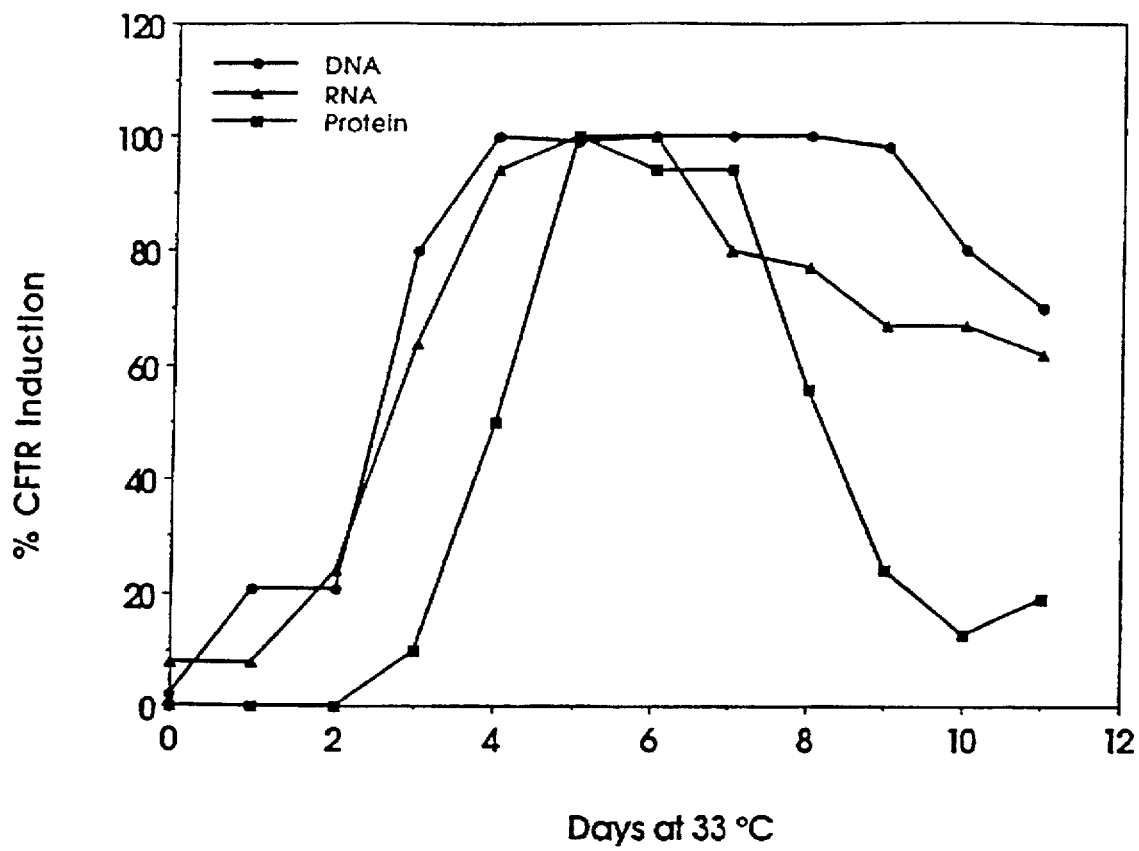
FIG. 5 is a graph depicting CFTR DNA, RNA, and protein levels in BTS cells transfected with CFTR cDNA and grown over a period of 11 days at 33° C.

The first expression system employed to study the effects of CFTR expression was a BTS (BCS-40 monkey cells transfected with tsA58 allele of SV40 large T antigen gene) cell system. Sasaki, R. and Ikura, K. eds. Animal Cell Culture and Production of Biologicals (Kluwer Academic Publishers 1991) 251–258. A monkey kidney cell line expressing a temperature sensitive SV40 large-T antigen was stably transfected at 39° C. with a plasmid containing CFTR cDNA (pCMV-CFTR-936c as shown in FIG. 3, see map of pRc/CMV (Invitrogen Corporation 1992 catalog for more detailed structure of pCMV 936c), the neo gene, and the SV40 origin of replication. Stable cell lines were isolated by G-418 selection and expanded at the non-permissive temperature (39° C.) (FIG. 4 Stage I). The cell line is shifted down to the permissive temperature for functional large-T antigen (33° C.). This is depicted in FIG. 4 as Stage II. Under permissive conditions, the integrated DNA replicates, excised from the chromosome, and amplifies to high copy number (up to thousand of copies per cell). The majority of the cells in culture undergo amplification. Sedivy, J. M. in Animal Cell Culture and the Production of Biologicals (Kluwar Academic Publishers, 1991) 251–258. The BTS cells were grown at 33° C. for 11 days. Protein lysates, total RNA and genomic DNA samples were isolated each day. Approximately 10 µg of genomic DNA was digested with EcoRI, electrophoresed on a 1% agarose gel, transferred to a nylon membrane, and hybridized with a 1.4 kb randomly primed fragment of pMT-CFTR. Total RNA was isolated by the guanidinium method, electrophoresed on a 1% agarose/ 10% formaldehyde gel, transferred to a nylon membrane, and hybridized with the 1.4 kb EcoRI-EcoRI fragment from pMT-CFTR. DNA and RNA were quantitated using a phosphoimager. Protein lysates (20 µg) were electrophoresed on a 4–15% Diacchi gel, transferred to immobilon and immunoblotted with anti-CFTR (24-1) antibody using the ECL detection method. As shown in FIG. 5, within 3 days of the shift to the permissive temperature, the integrated cDNA (gene expressing CFTR) is amplified by up to 100 copies. Concomitant with this was a 100 fold increase in CFTR RNA and protein levels. CFTR expression reached maximum concentrations by day 5. The induction of CFTR protein was temporary and decreased dramatically between days 7 and 8. This expression profile has not been observed for other proteins expressed in the BTS system. DNA and CFTR expression decreased over time after induction at 33° C. However, the decrease in DNA copy number and RNA concentrations occurred later and to a lesser extent than the observed decrease in CFTR. These results suggest that CFTR expression is unstable in BTS cells and that the major point of down-regulation is at the level of protein expression.

Figure 6:
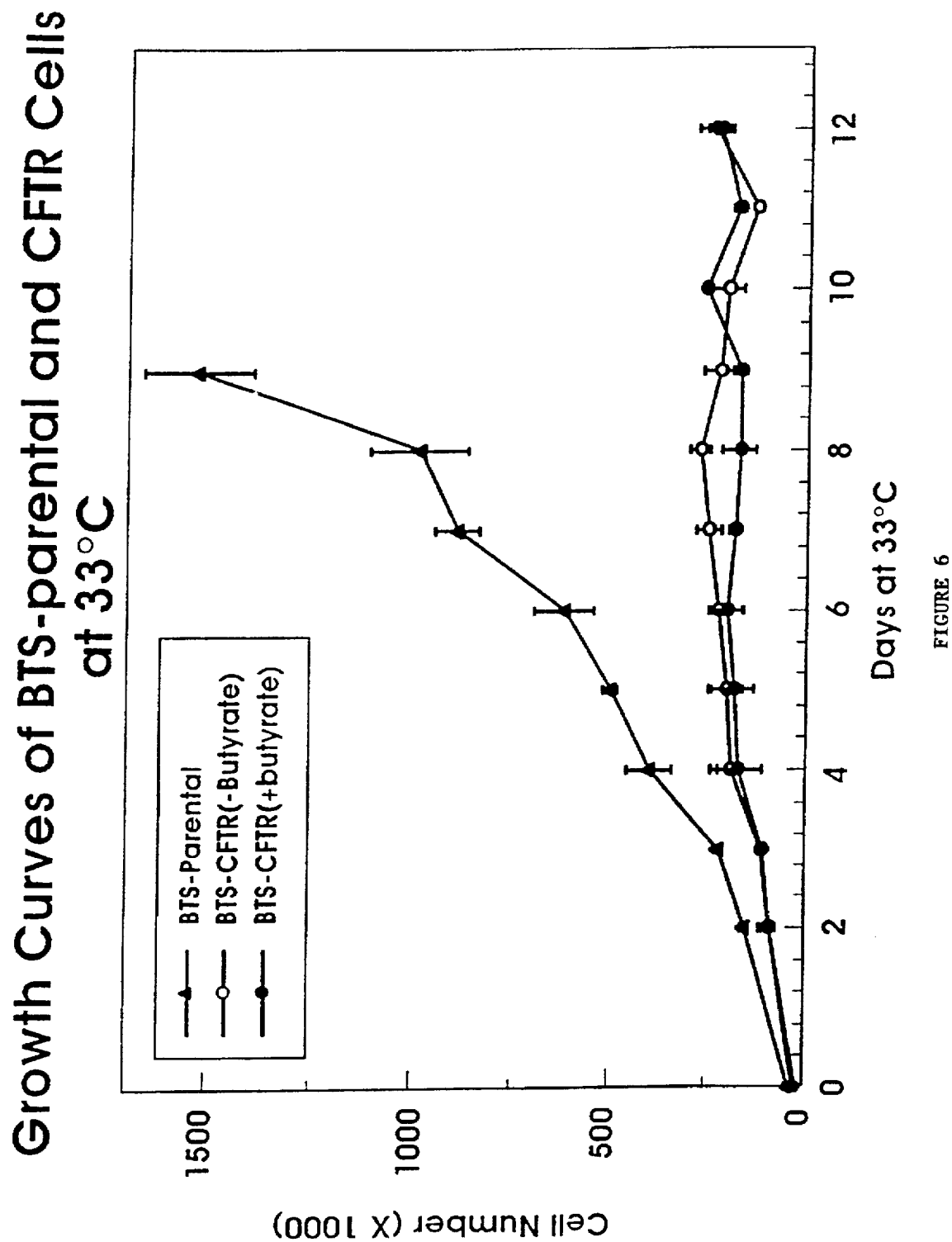
FIG. 6 is a graph demonstrating growth curves of BTS-parental and BTS-CFTR cells at 33° C. (the permissive temperature for functional large T antigen). BTS-parental and BTS-CFTR grow at similar rates at 39° C. When the temperature is shifted to 33° C., BTS-parental cells continue to grow albeit at a slower rate. In contrast, BTS-CFTR cells growth arrest within 5 days of shift to 33° C.

FIG. 6 is a graph depicting growth curves for BTS-parental and BTS-CFTR cells at 33° C. Cells were plated at a density of $2 \times 10^5$ in 60 mm dishes an incubated at 39° C. or 33° C. for various times. Cells were harvested with trypsin, resuspended and counted using a hemocytometer. Counts were done in triplicate iota replicate plates. The data depicted in FIG. 6 represents the mean ±SEM. BTS-parental and BTS-CFTR grow at similar rates at 39° C. When shifted to 33° C., BTS-parental cells continue to grow albeit at a slower rate. In contrast, BTS-CFTR cells growth arrest within 5 days of shift to 33° C. Examination of the cell growth properties revealed a correlation between high CFTR expression in growth arrest of the cells.

Figure 7:
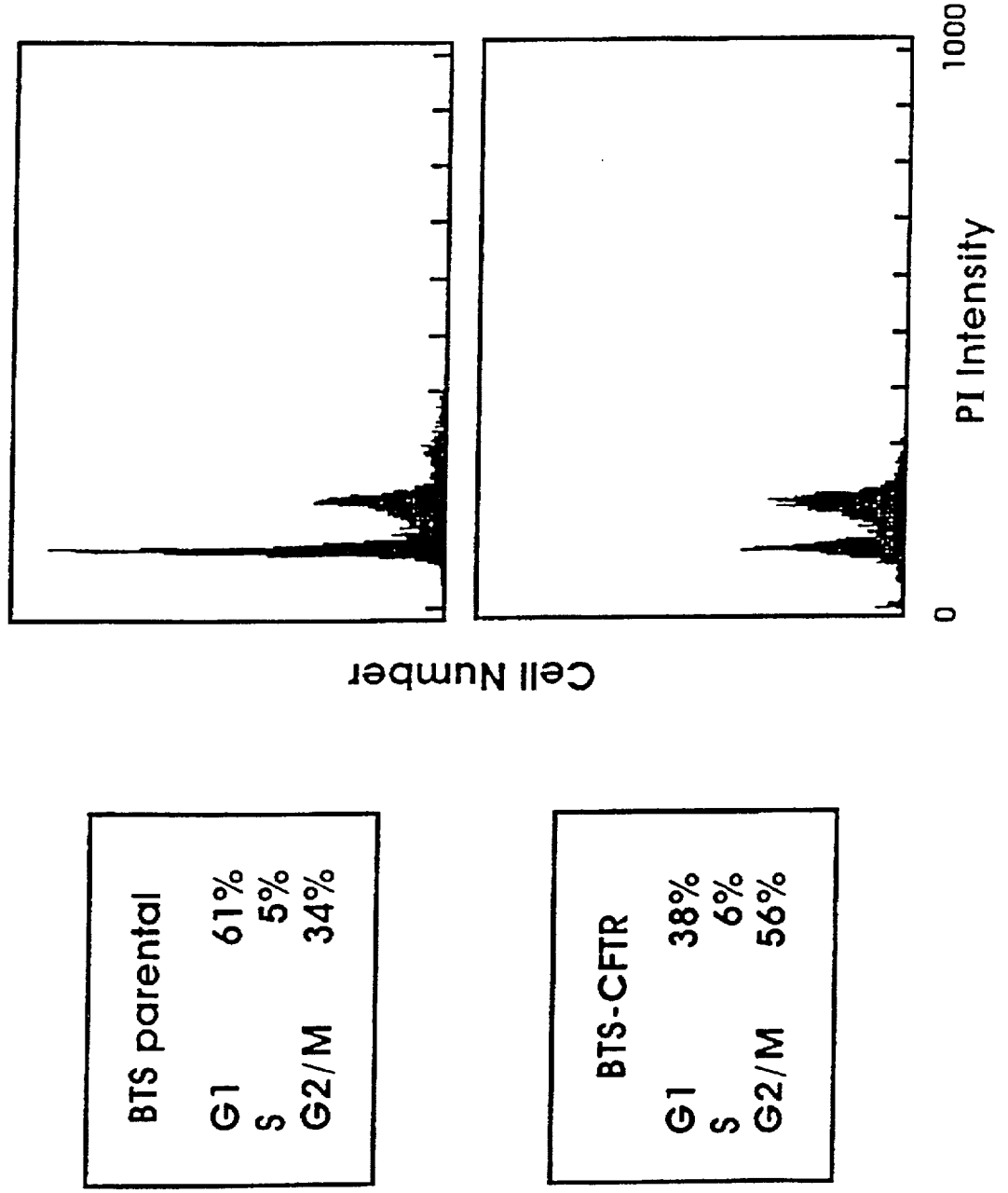
FIG. 7 depicts a cytofluorographic analysis of DNA from BTS-parental and BTS-CFTR cells. BTS-parental cells showed a profile that is consistent with log phase growth. In contrast, there was an increase in the number of BTS-CFTR cells in the G2 stage of the cell cycle suggesting that BTS-CFTR cells arrest in G2 upon CFTR expression.
Figure 8:
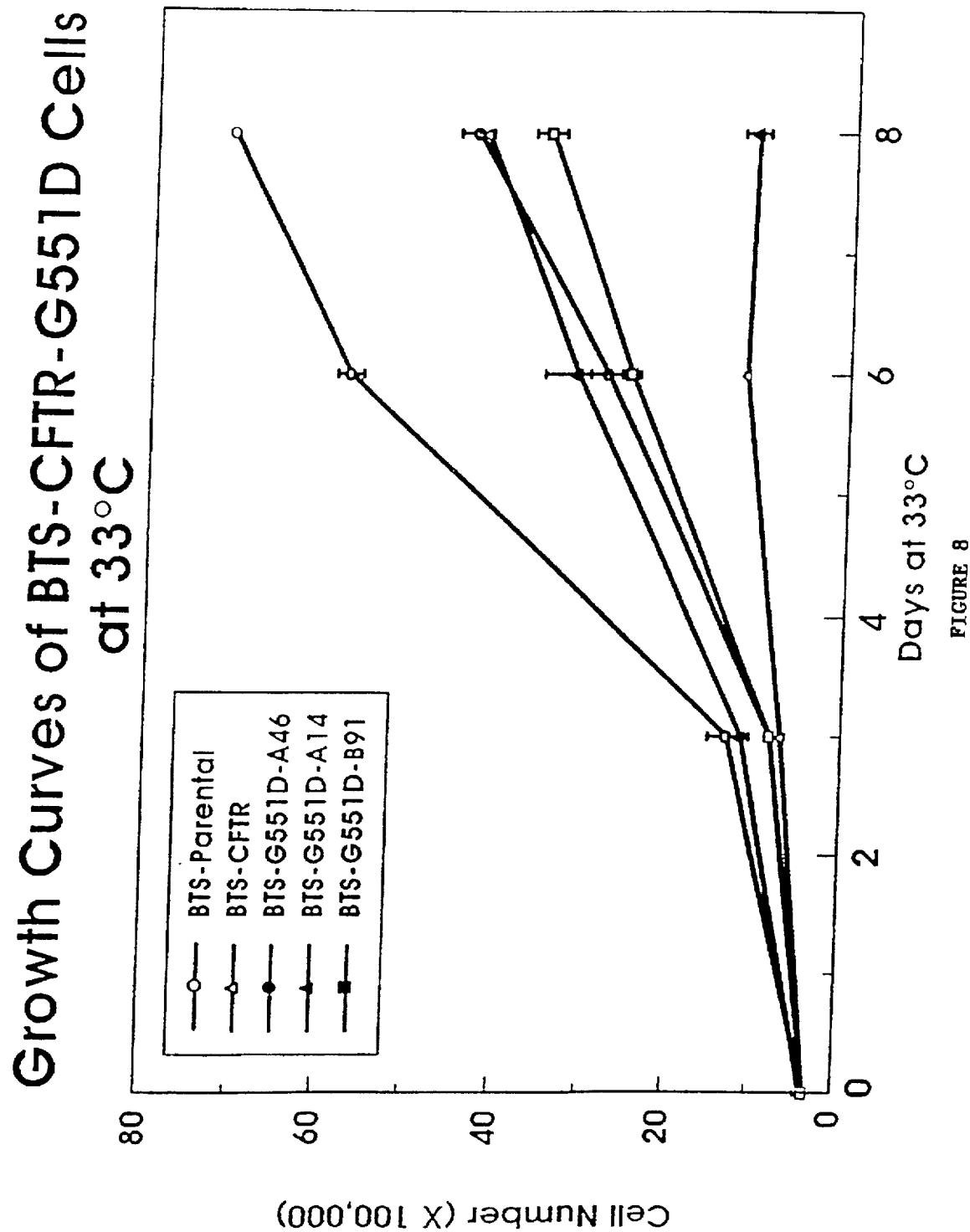
FIG. 8 is a graph demonstrating growth curves of BTS-parental, BTS-CFTR, and BTS-G551D mutants (the G551D mutation results in the synthesis of a CFTR variant that is post-translationally processed and delivered to the plasma membrane but whose Cl⁻ channel activity is severely defective). Unlike the BTS-CFTR cells, the BTS-G551D cells continued to grow at the permissive temperature but at a slightly lower rate than BTS-parental cells.

FIG. 7 shows cytofluorographic analysis of the cells expressing CFTR. BTS-parental and CFTR lines were grown at 33° C. for 5 days, harvested in the presence of EDTA and ethanol fixed. DNA was stained with 7-AAD and DNA content analyzed by cytofluorography. BTS-parental cells showed a profile that is consistent with log phase growth. In contrast, there was an increase in the number of BTS-CFTR cells in the G2 stage of the cell cycle suggesting that BTS-CFTR arrest in G2 upon CFTR expression. The G551D mutant form of CFTR, however, was not growth arrested at 33° C. The G551D mutant form of CFTR was introduced into BTS cells. Protein expression is temperature inducible. Cell counts were done as described above for FIG. 7. As demonstrated by the graph in FIG. 8, BTS-CFTR G551D cells continued to grow at the permissive temperature but at a slightly lower rate than BTS-parental cells.

Figure 9:
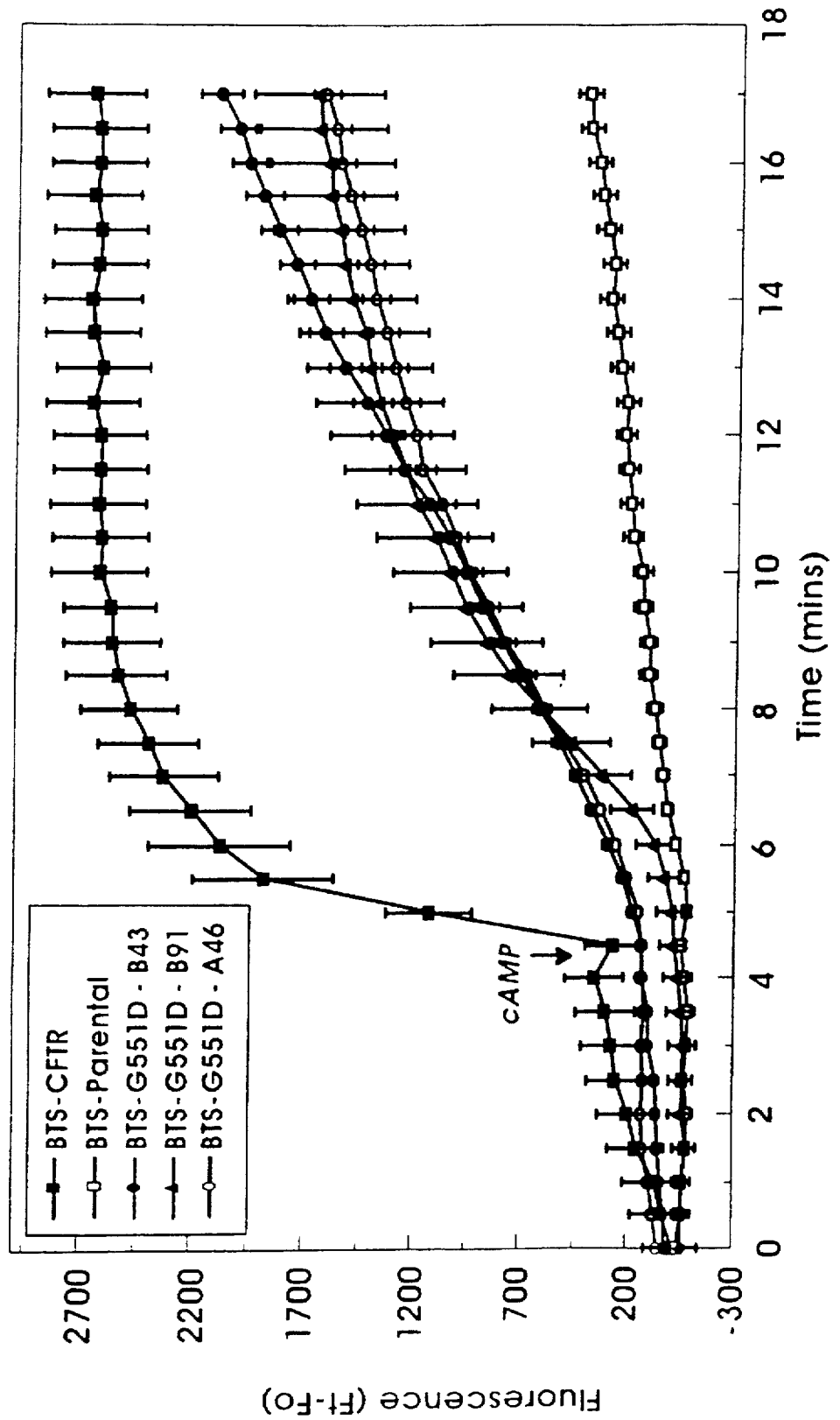
FIG. 9 shows the results of a single-cell membrane halide assay using the Cl⁻ indicator dye SPQ halide efflux assay of BTS-parental, BTS-G551D, and BTS-CFTR cells on day 5 at 33° C. The change in fluorescence of SPQ is shown for BTS CFTR cells (n=11, when n=number of cells), BTS-parental (n=15), BTS-G551D, clone B43 (n=30), BTS-G551D, clone B91 (n=11) and BTS-G551D, clone A46 (n=28). NO₃— was substituted for Cl⁻ in the bathing solution at 0 min. Four minutes later (at the arrow), cells were stimulated with 20 µM forskolin and 100 µM IBMX to increase intracellular levels of cAMP. Data are mean ±SEM of fluorescence ($F_o$, average fluorescence measured in the presence of Cl⁻ for 2 min prior to ion substitution). Expression of wild type CFTR confers cAMP-dependent Cl⁻ channels in BTS cells. The variant G551D exhibits measurable but nevertheless severely defective Cl⁻ channel activity.

To ascertain the functionality of CFTR in the newly generated cell lines, a single-cell membrane halide permeability assay using the Cl⁻ indicator dye SPQ was used. Cheng, S. H. et al. (1991) *Cell* 66:1027–1036. In this assay, an increase in the rate of change of SPQ fluorescence reflects an increase in halide permeability. The change in fluorescence of SPQ is shown in FIG. 9 for BTS-CFTR cells (n=11, wherein n=number of cells), BTS-parental (n=15), BTS-G551D, clone B43 (n=30), BTS-G551D, clone B91 (n=11) and BTS-G551D, clone A46 (n=28). $NO_3^-$ was substituted for Cl⁻ in the bathing solution at 0 minutes. Four minutes later (at the arrow), cells were stimulated with 20 µM forskolin and 100 µM IBMX to increase intracellular levels of cAMP. Data are mean ±SEM of fluorescence at time t ($F_t$) minus the baseline fluorescence ($F_o$, average fluorescence measured in the presence of Cl⁻ for 2 minutes prior to ion substitution). Expression of wild-type CFTR confers cAMP-dependent Cl⁻ channels in BTS cells. The variant G551D exhibits measurable but severely defective Cl⁻ channel activity.

Second Expression System: Transgenic Rabbits

Superovulation was induced in twenty-six female New Zealand White donor rabbits by intramuscular injection with 150 units of Pregnant Marc's Serum Gonadotropin (PMSG) followed 72 hours later with 150 units of human chorionic gonadotropin IV (HCG IV). The females were bred at least twice to a proven buck. Fifty-four recipient females were bred at least twice with a vasectomized buck and injected with 150 traits of HCG IV to synchronize ovulation with that of the donor rabbits. Nineteen hours following mating, the donor rabbits were anesthetized by intramuscular injection of 1.5 cc of acepromazine/ketamine (1 mg/ml/10 mg/ml) and the mid-ventral abdominal area was shaved, washed with Betadine scrub, sprayed with Betadine solution, and draped in preparation for surgery. A mid-ventral incision was made using sterile surgical equipment. The oviducts were exteriorized and fertilized one-cell embryos flushed therefrom using sterilized phosphate buffered saline (PBS) and collected. The donor embryos were microinjected with a construct containing either the wild type CFTR cDNA, a nonglycosylated variant of CFTR cDNA, or CFTR variant G551D cDNA cloned downstream of the goat β-casein promoter as described above and reimplanted in both oviducts of recipient rabbits by flank incision. During the first week after birth, tissue from offspring was collected by cutting a small piece of the ear for PCR analysis.

Figure 10:
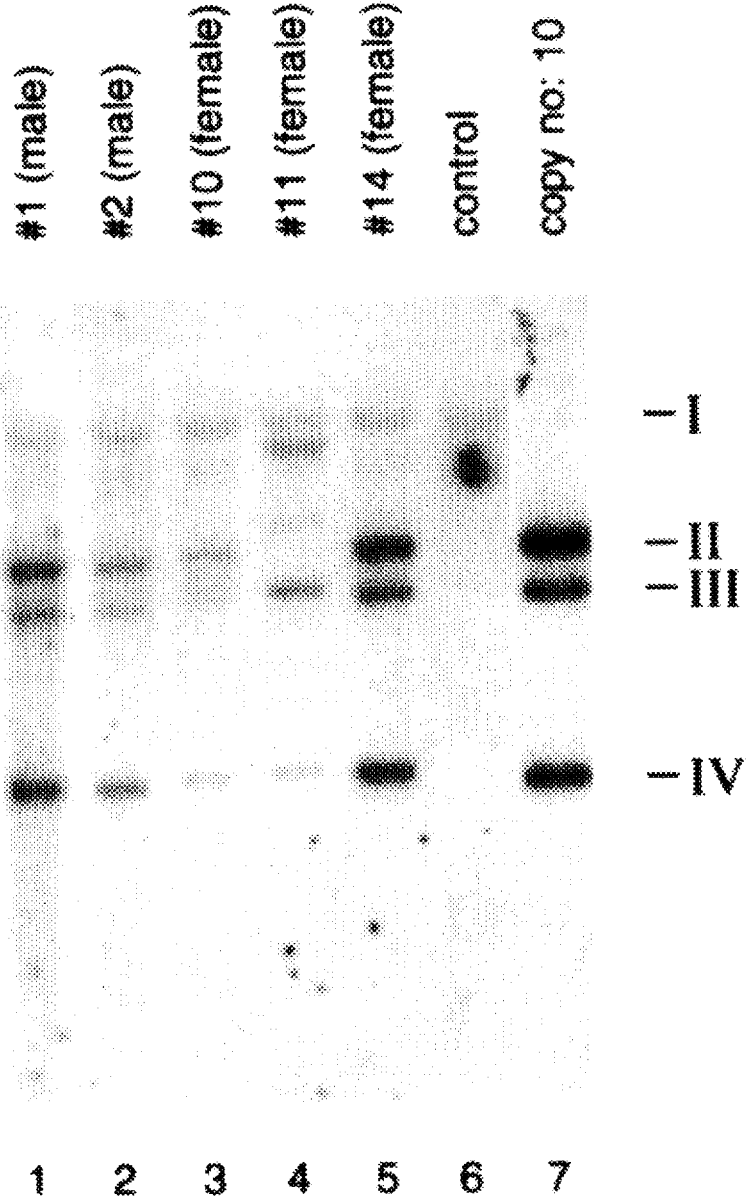
FIG. 10 depicts identification of positive transgenic rabbits by Southern blot analysis. Band I is rabbit β-casein DNA and bands II, III and IV are CFTR DNA. Lane 6 is a control rabbit and lanes 1 to 5 show results of five founder transgenic rabbits. Lane 7 indicates the signal observed for 10 copies of CFTR DNA. Copy number was quantitated using a Betascope 603 analyzer. Copy number of the transgene in the lines varied between 1 and 10.

Transgenic rabbits were identified by Southern blot analysis of DNA from the ears of resulting offspring. Briefly, approximately 15 µg of genomic DNA from each founder rabbit was digested with EcoRI, separated on a 1% agarose gel, transferred to magnagraph nylon (Fisher Scientific) and hybridized with the 384 bp Pvu II-Pvu II fragment from exon 7 of the goat β-casein cDNA (Yoshimura, M. et al. (1986) *Nucleic Acids Res.* 14:8224) and the 4.5 kb SalI-SalI fragment of pMT-CFTR. Copy number was quantitated using a Betascope 603 Analyzer. FIG. 10 shows DNA from the positive founder animals. Band I is rabbit β-casein DNA and bands II, III and IV are CFTR DNA. Lane 6 is a control rabbit and lanes 1 to 5 show results of five founder transgenic rabbits. Lane 7 indicates the signal observed using a Betascope 603 analyzer. Such analysis indicates the copy number of the transgene in the lines varied between 1 and 10.

Observed Lethality of CFTR Expression in Male Transgenic Rabbits

It was discovered that male transgenic rabbits which developed from the embryos that were injected with a construct containing wild type CFTR cDNA or a nonglycosylated variant of CFTR cDNA were still born or died soon after birth. FIG. 12 shows a table demonstrating lethality of CFTR expression to male transgenic rabbits. The column under "Dead" represents animals that were stillborn or that died soon after birth. As shown in FIG. 12, all of the founder male transgenic rabbits containing wild type CFTR transgene were non-viable. The selective lethality observed in male rabbits was also manifest in the F1 generation but at a lower penetrance. Transgenic rabbits containing the nonglycosylated variant also displayed selective male lethality in both founders and F1 animals but at reduced potency. In contrast to the observed lethality in male transgenic rabbits that contained either wild type or nonglycosylated CFTR cDNA, male transgenic rabbits that contained CFTR variant G551D cDNA were born viable. See FIG. 13. The G551D mutation results in the synthesis of a variant that is post-translationally processed and delivered to the plasma membrane but whose Cl⁻ channel activity is severely defective. To date, no lethality has been observed in the founder animals beating the G551D-CFTR transgene, leading to the conclusion that the male lethality observed in transgenic rabbits is a consequence of the Cl⁻ channel activity of wild type CFTR.

Production of CFTR in Milk of Female Transgenic Rabbits

Founder rabbits were bred to produce lactating transgenic females. Milk from such animals was collected, diluted 10-fold with PBS and treated with RIPA (50 mM Tris-HCl [pH 7.5], 150 mM NaCl, 1% Triton X-100, 1% sodium deoxycholate and 0.1% sodium dodecyl sulphate) buffer to solubilize membrane proteins. Rabbits were injected with oxytocin and milked 5 minutes later with a suction device. Briefly, samples were examined for the presence of CFTR by immunoprecipitation with the monoclonal antibody mAb 24-1 (U.S. Ser. No. 08/114,950, filed Aug. 27, 1993), followed by in vitro phosporylation treatment of the washed immunoprecipitate with protein kinase A (PKA) in the presence of [γ³²P]ATP. Gregory, R. J. et al. (1990) *Nature* 347:382–386; Cheng, S. H. et al. (1990) *Cell* 63:827–834. More specifically, procedures for preparing cell lysates, immunoprecipitation of proteins using anti-CFTR antibodies, one-dimensional peptide analysis and SDS-polyacrylamide gel electrophoresis were as described by Cheng et al. Cheng, S. H. et al. (1990) *Cell* 63:827–834; Cheng, S. H. et al. (1991) *Cell* 66:1027–1036. In vitro phosphorylation of the CFTR-containing immunoprecipitates was achieved by incubating with protein kinase A and [γ³²P]ATP (10 µCi) in a final volume of 50 µl in kinase buffer (50 mM Tris-HCl, pH 7.5, 10 mM $MgCl_2$ and 100 µg ml⁻¹ bovine serum albumin) at 30° C. for 60 min.

Figure 11:
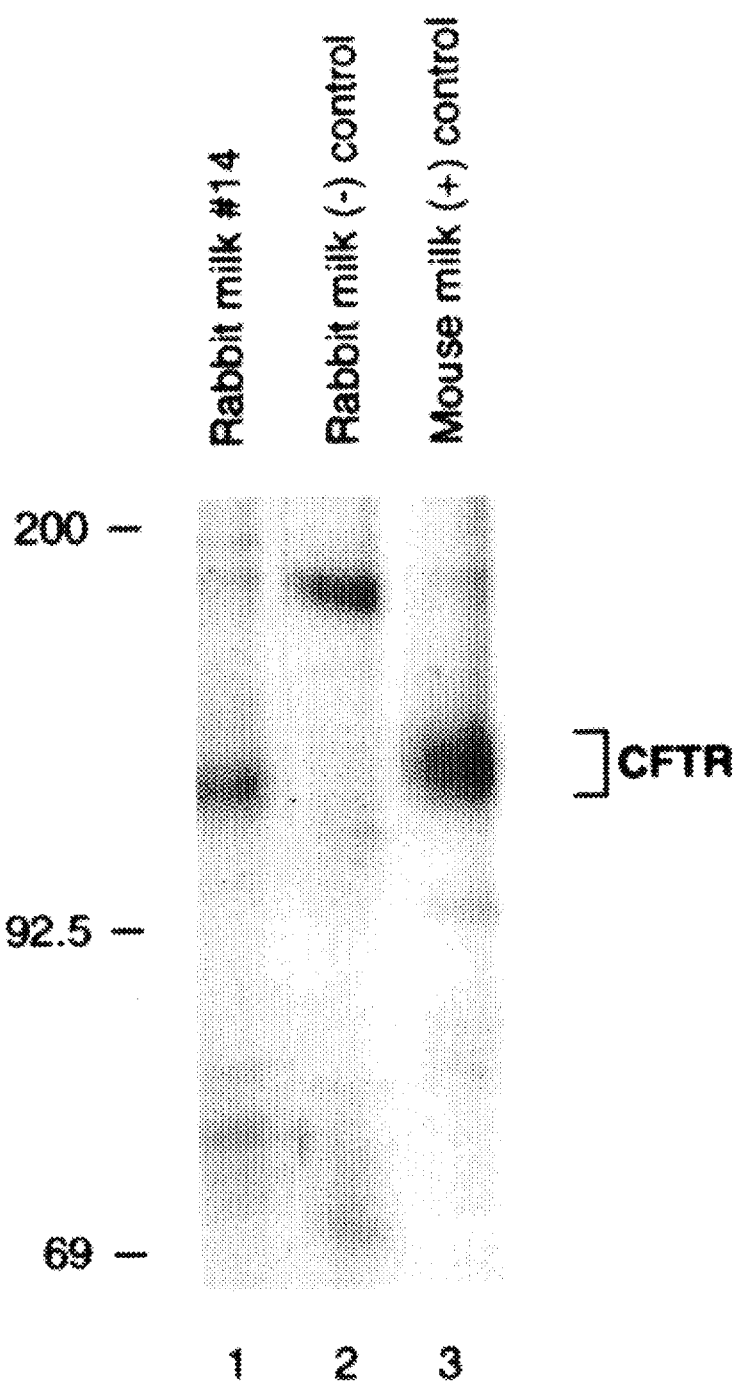
FIG. 11 depicts detection of CFTR in milk of transgenic rabbits using monoclonal antibody mAb 24-1. Lane 1 contains 50 µl of milk from transgenic rabbit #14, lane 2, 50 µl of milk from control rabbit and lane 3, 50 µl of milk from a CFTR transgenic mouse (DiTullio, P. et al. (1992) Bio/Technology 10(1):74–77)

FIG. 11 shows a polyacrylamide gel of samples from milk of rabbit #14, of a control rabbit and milk from a CFTR transgenic mouse. DiTullio, P. et al. (1992) *Bio/Technology* 10(1): 74–77. Lane 1 contains 50 µl of milk from transgenic rabbit #14, lane 2 contains 50 µl of control milk, lane 3 contains 50 µl of milk from a CFTR transgenic mouse. The position of CFTR is indicated on the right margin. Exposure time was 30 minutes at −70° C. As can be seen from the results, expression levels of CFTR in the milk of transgenic rabbits is low. Detectable CFTR was only observed in rabbit #14. Based on estimates of the amount of CFTR in the transgenic mouse milk, approximately 0.01–0.1 µg of CFTR is present per ml of rabbit #14 milk.

Example 3

Identification of Consensus Sequences in Human CFTR cDNA which Correspond to Androgen Responsive Elements Consensus sequences for androgen responsive elements were derived from published reports. Roche, P. J. et al. (1992) *Mol. Endocrinol.* 6:2229–2235; Claessens, F. et al. (1990) *Mol. Cell Endocrinol.* 74:203–212. The androgen responsive element sequences are aligned with human CFTR cDNA using a bestfit analysis from the Genetics Computer Group sequence analysis software package or the IBI sequence analysis software for MacVector and CFTR cDNA consensus sequences are determined. FIG. 14 shows an example of a consensus sequence in human CFTR cDNA which corresponds to an androgen responsive element. Steroid hormones, such as androgens, regulate transcription by binding to specific intracellular receptors which then interact with steroid hormone response elements. Such elements are cis-acting DNA sequences that have the properties of transcriptional enhancers. Several such elements present in the coding sequence of human CFTR are described above under the definition of "hormone responsive element". These elements can inappropriately augment CFTR expression in certain tissues during fetal development in response to androgens.

Example 4

Confirmation of Presence of Hormone Responsive Elements in Human CFTR cDNA

Different experiments can be conducted in order to confirm that consensus sequences in human CFTR cDNA which correspond to androgen responsive elements are androgen responsive elements. For example, human CFTR cDNA can be cloned into a mammalian expression vector (e.g., pREP4, Invitrogen, San Diego, Calif.) and transfected into an androgen responsive cell line such as ZR-71 cells (Roche, P. J. et al. (1992) *Mol. Endocrinol.* 6:2229–2235) or DDT-MF-2 cells (ATCC CRL 1701) ((1983) *In Vitro* 19:929–936). The transfected cells can then be treated with testosterone and assayed for an increase in CFTR expression. An increase in CFTR expression in response to androgen treatment indicates the presence of an androgen responsive element in the CFTR cDNA.

Another experiment that can be conducted in order to confirm that consensus sequences in human CFTR cDNA which correspond to hormone responsive elements are hormone responsive elements is to determine if the hormone receptor binds to putative hormone responsive elements in the human CFTR cDNA. Such an experiment can be performed by gel isolating overlapping fragments of the CFTR cDNA and using the fragments in a mobility shift assay (Roche, P. J. et al. (1992) *Mol. Endocrinol.* 6:2229–2235). Binding of the hormone receptor to a CFTR cDNA fragment will cause a shift in the electrophoretic mobility on a polyacrylamide gel of the DNA containing the hormone responsive element. The CFTR cDNA fragments containing hormone responsive elements can thereby be detected.

Example 5

Inactivation of Hormone Responsive Elements in Human CFTR cDNA

Inactivation of a hormone responsive element can be brought about by alteration of the nucleotide sequence of the responsive element located in the CFTR cDNA. Site-directed mutagenesis can be used to generate nucleotide alterations, such as nucleotide deletion, addition, or substitution, in the hormone responsive elements located in CFTR cDNA. Such methods include, among others, a polymerase chain reaction (PCR) with oligonucleotide primers bearing one or more mutations (oligonucleotide-mediated mutagenesis). Sambrook, J. et al. Molecular Cloning: A Laboratory Manual (Cold Spring Harbor Laboratory Press 1989)). For example, nucleotides 2988 to 3002 (5' GTTA-CATTCTGTTCT 3') (SEQ ID NO:3) of human CFTR cDNA can be mutated to (5' GCTGCATTCCGTGCT 3')) (SEQ ID NO:8) using site-directed mutagenesis. Once alteration of the nucleotide sequence of the hormone responsive element in the CFTR cDNA has been accomplished, the cDNA can be cloned into a lung surfactant promoter construct (SPC) (Whitsett, J. A. et al. (1992) *Nature Gen.* 2:13–20) to confirm that the hormone responsive element has been inactivated. This lung SPC promoter has been characterized as a tightly regulated tissue specific promoter except when directing the expression of CFTR cDNA. High levels of human CFTR have been detected in the testes of transgenic mice carrying the SPC-CFTR transgene, possibly due to the presence of an androgen responsive element. Whitsett, J. A. et al. (1992) *Nature Gen.* 2:13–20. Transgenic mice carrying an SPC CFTR transgene in which the androgen responsive element was mutagenized should show no expression in the testes and confirm inactivation of the androgen responsive element. Alternatively, the same CFTR cDNA can be cloned into the goat β-casein vector described in Example 1 and microinjected into rabbit embryos. The birth of normal male offspring would confirm that the androgen responsive element in the cDNA is inactivated. Yet another method of confirming inactivation of hormone responsive elements in CFTR cDNA is described above in Example 4. Briefly, the CFTR cDNA containing, for example, an androgen responsive element can be cloned in a mammalian expression vector and transfected into an androgen responsive cell line. The cell line can then be treated with an androgen, such as testosterone, and assayed for a CFTR expression. CFTR expression can be compared to the CFTR expression in androgen responsive cells transfected with a known androgen responsive element that have been treated with an androgen. If there is a decrease in CFTR expression in the androgen responsive cell line that has been transfected with the CFTR cDNA containing a mutated androgen responsive element relative to CFTR expression in androgen responsive cells transfected with a known androgen responsive element that have been treated with an androgen, it is an indication that the androgen responsive element has been inactivated.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. Recombinant DNA comprising a nucleic acid sequence, the sequence including:

a consensus sequence of at least one hormone responsive element, wherein the consensus sequence is mutated to render said hormone responsive element inactive; and a sequence encoding a membrane-associated protein.

2. The DNA of claim 1 wherein the consensus sequence is located within the sequence encoding the membrane-associated protein.

3. The DNA of claim 1 wherein the membrane-associated protein is cystic fibrosis transmembrane conductance regulator.

4. The DNA of claim 2 wherein the membrane-associated protein is cystic fibrosis transmembrane conductance regulator.

5. The DNA of claim 1 wherein the hormone responsive element is a steroid hormone responsive element.

6. The DNA of claim 5 wherein the steroid hormone responsive element is a glucocorticoid responsive element.

7. The DNA of claim 5 wherein the steroid hormone responsive element is an androgen responsive element.

8. The DNA of claim 4 wherein the consensus sequence is selected from the group of nucleotide sequences consisting of SEQ ID NO:3, SEQ ID NO:4, SEQ ID NO:5, SEQ ID NO:6 and SEQ ID NO:7.

9. The DNA of claim 8 wherein the consensus sequence is an androgen responsive element.

10. The DNA of claim 1 wherein the mutation comprises nucleotide substitution, addition or deletion.

11. A cystic fibrosis-affected cell comprising the DNA of claim 1.

* * * * *